(12) United States Patent
Yang et al.

(10) Patent No.: US 7,960,609 B2
(45) Date of Patent: Jun. 14, 2011

(54) PLANT VECTOR PBSNB-TEV, VECTORS DERIVED THEREFROM, AND METHODS OF USE

(75) Inventors: Joo-Sung Yang, Seocho-gu (KR); Eun Hee Yang, Busan (KR)

(73) Assignee: Sungkyunkwan University Foundation for Corporate Collaboration, Gyeonggi-do (KR)

( * ) Notice: Subject to any disclaimer, the term of this patent is extended or adjusted under 35 U.S.C. 154(b) by 365 days.

(21) Appl. No.: 12/297,205

(22) PCT Filed: Oct. 1, 2007

(86) PCT No.: PCT/KR2007/004802
§ 371 (c)(1),
(2), (4) Date: Oct. 14, 2008

(87) PCT Pub. No.: WO2009/008573
PCT Pub. Date: Jan. 15, 2009

(65) Prior Publication Data
US 2011/0059129 A1    Mar. 10, 2011

(30) Foreign Application Priority Data
Jul. 10, 2007    (KR) .................. 10-2007-0069373

(51) Int. Cl.
*C12N 15/82* (2006.01)
*C12N 5/04* (2006.01)
*C12N 5/10* (2006.01)
*A01H 5/00* (2006.01)
*C07H 21/04* (2006.01)

(52) U.S. Cl. ........ 800/288; 800/278; 800/294; 800/295; 800/298; 800/307; 800/309; 800/317.2; 800/320; 800/320.2; 800/320.3; 435/320.1; 435/419; 536/23.1; 536/23.72; 536/24.1

(58) Field of Classification Search .................. None
See application file for complete search history.

(56) References Cited

U.S. PATENT DOCUMENTS
2005/0048074 A1    3/2005    Cardineau et al.
2007/0107086 A1    5/2007    Mihaliak et al.

FOREIGN PATENT DOCUMENTS
KR    10-2006-0029214    4/2006

OTHER PUBLICATIONS

Marquet-Blouin et al. Neutralizing immunogenicity of transgenic carrot (*Daucus carota* L.)—derived measles virus hemagglutinin. (2003) Plant Molecule Biology; vol. 51; pp. 459-469.*
James et al. Production and Characterization of biologically active human GM-CSF secreted by genetically modified plant cells. (2000) Protein Expression and Purification; Vo. 19; pp. 131-138.*
James et al., "Production and Characterization of Biologically Active Human GM-CSF Secreted by Genetically Modified Plant Cells," Protein Expression and Purification, 19:131-138 (2000).

* cited by examiner

*Primary Examiner* — Cathy Kingdon Worley
(74) *Attorney, Agent, or Firm* — Casimir Jones, S.C.

(57) ABSTRACT

The present invention relates to an avian influenza vaccine of plant origin, prepared by transforming a plant with a surface protein of avian influenza virus, hemagglutinin (HA) or neuraminidase (NA), and a method for preparing the same. Further, the present invention relates to an oral vaccine for preventing avian influenza virus, of which mass-production conditions are established, and thus the produced transgenic plant can be more easily, safely, and economically used as a fodder additive. Furthermore, the present invention relates to a reagent for diagnosing avian influenza virus infection, prepared by isolating and purifying a recombinant antigen protein from the transgenic plant.

18 Claims, 14 Drawing Sheets

[Fig. 1]
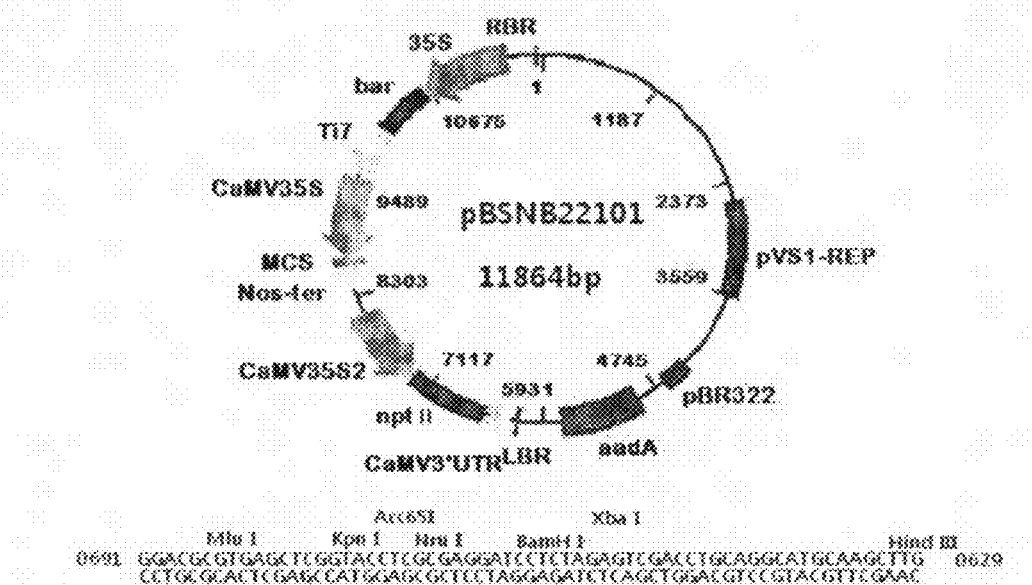
[Fig. 2]
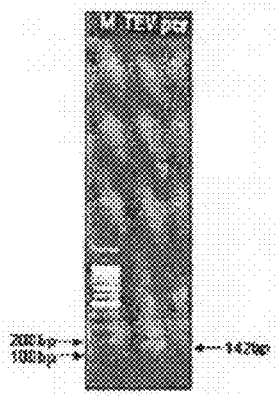
[Fig. 3]
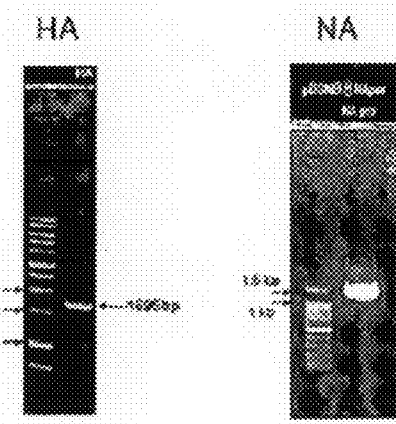

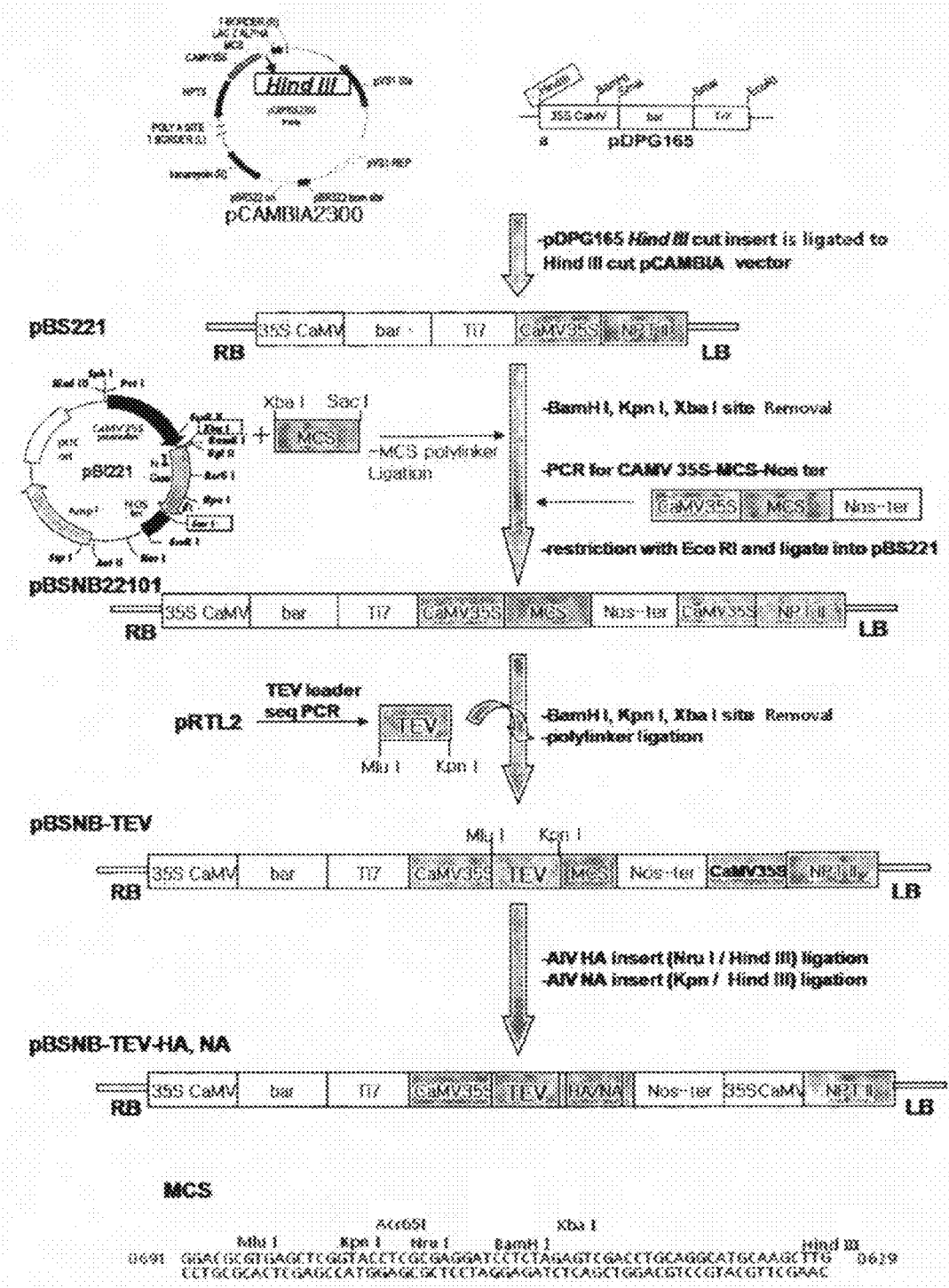

[Fig. 5]
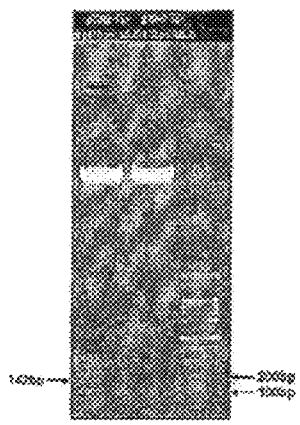
[Fig. 6]
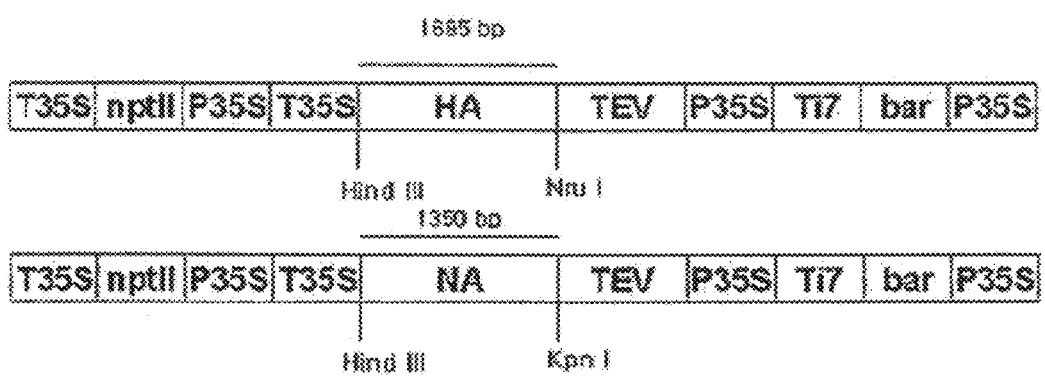
[Fig. 7]
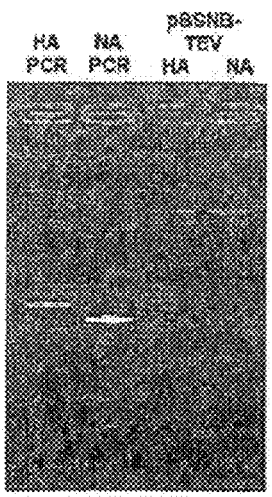

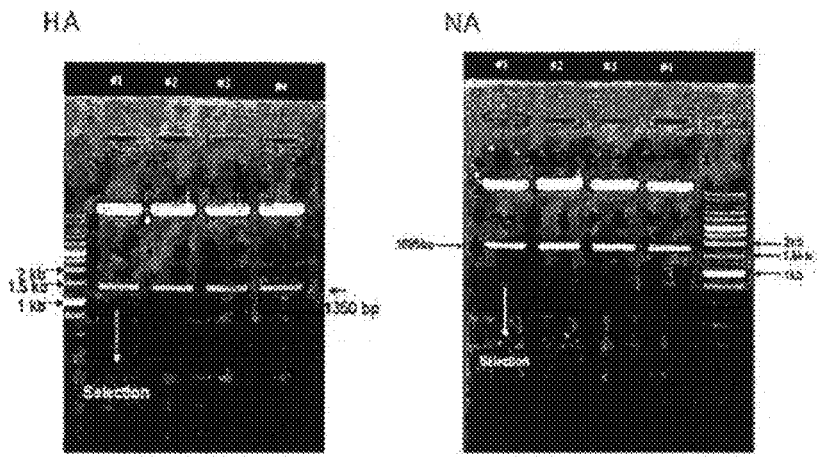

[Fig. 11]
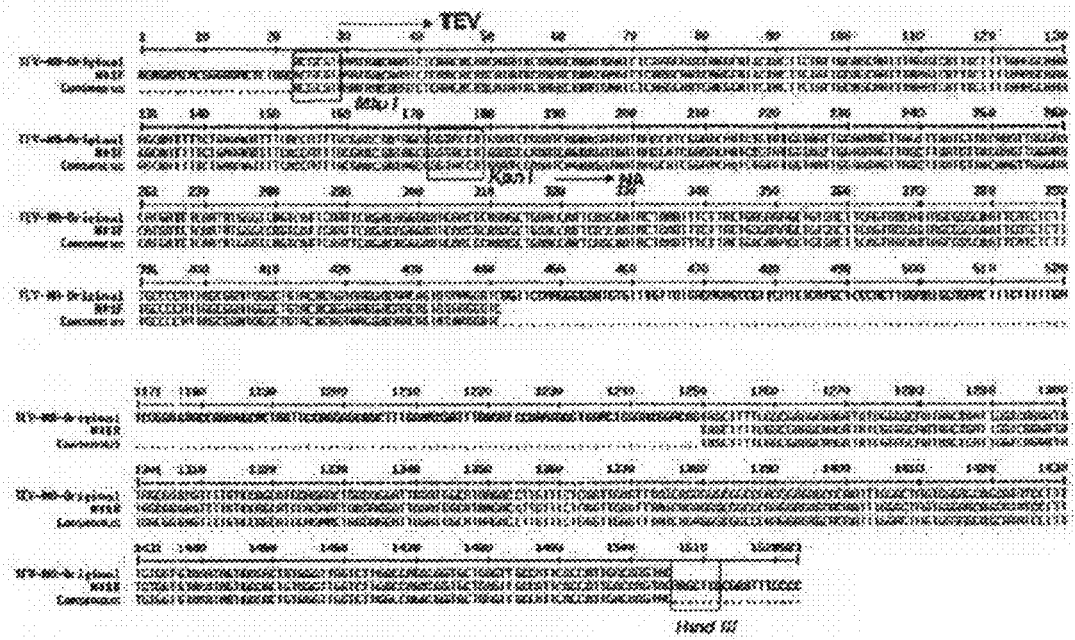
[Fig. 12]
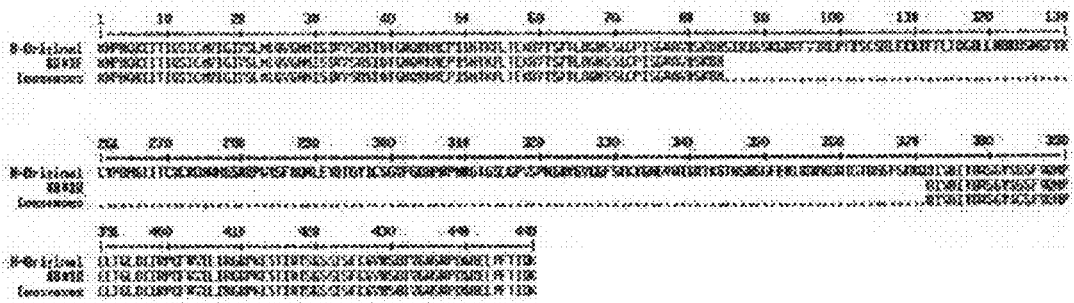

[Fig. 13]
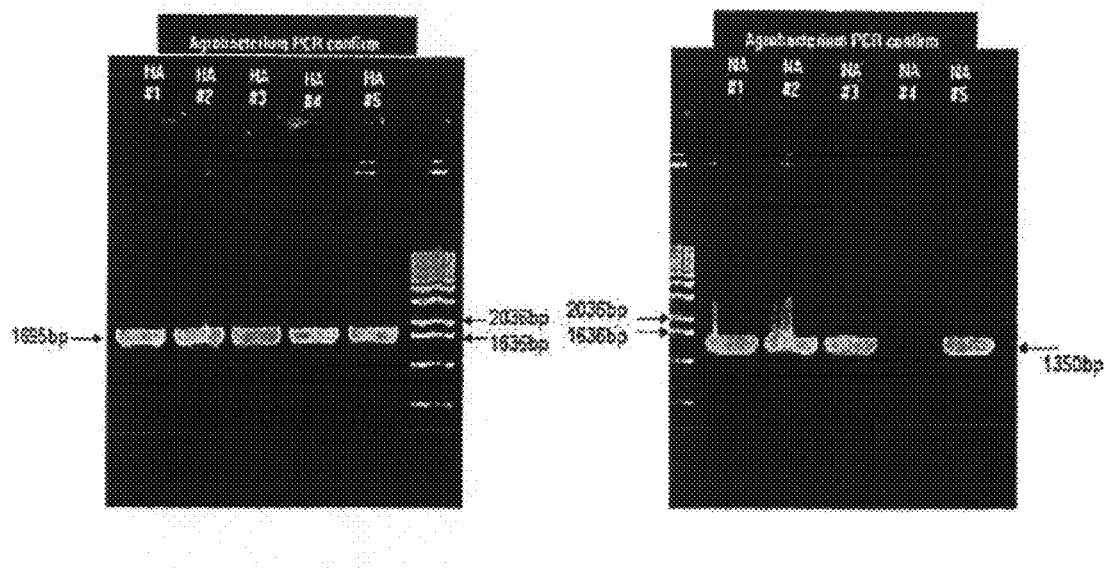
[Fig. 14]
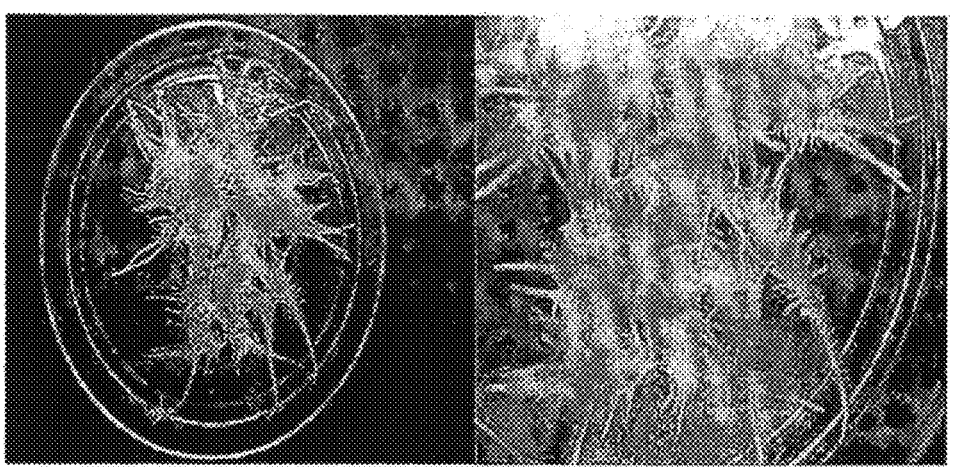

[Fig. 15]
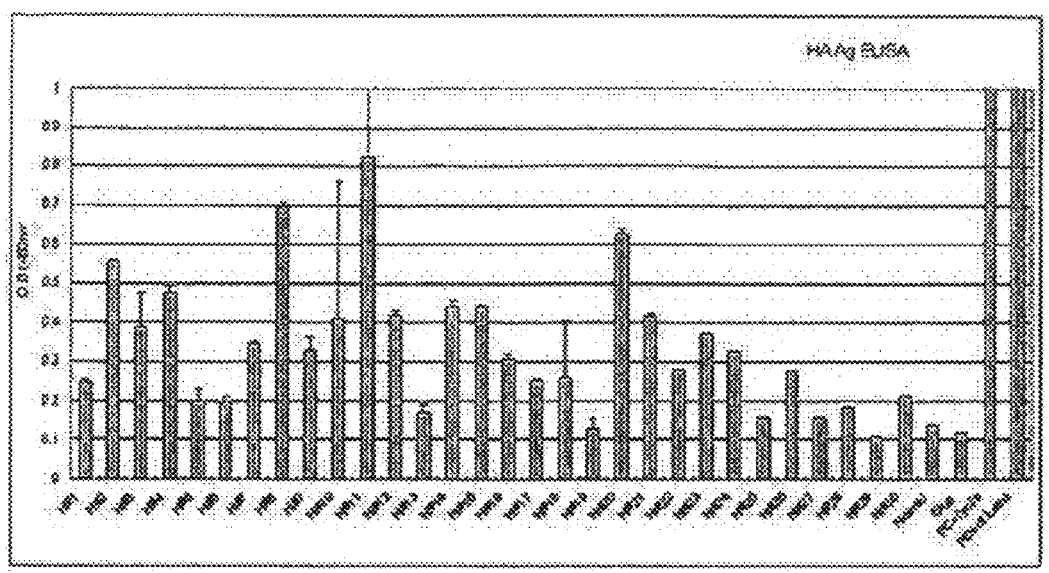

[Fig. 16]
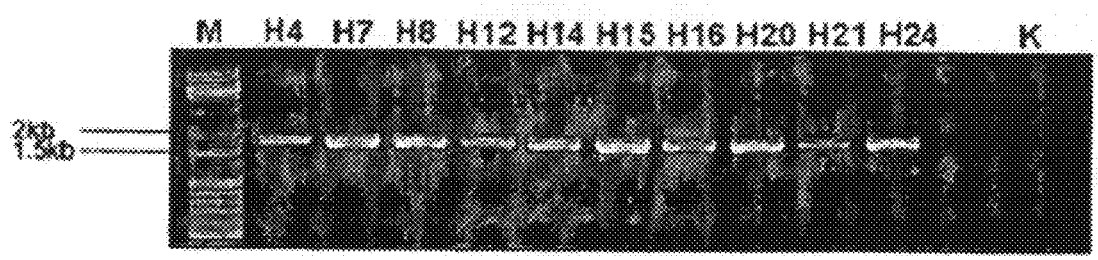
[Fig. 17]
a)
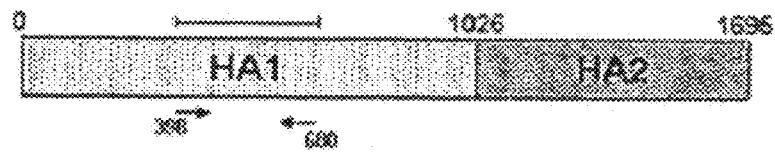
b)
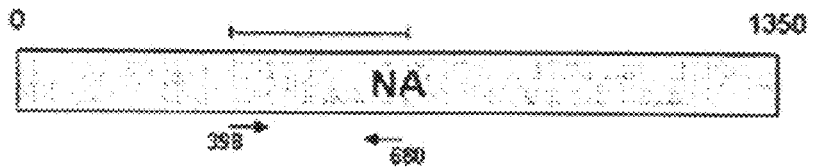

[Fig. 18]
a)
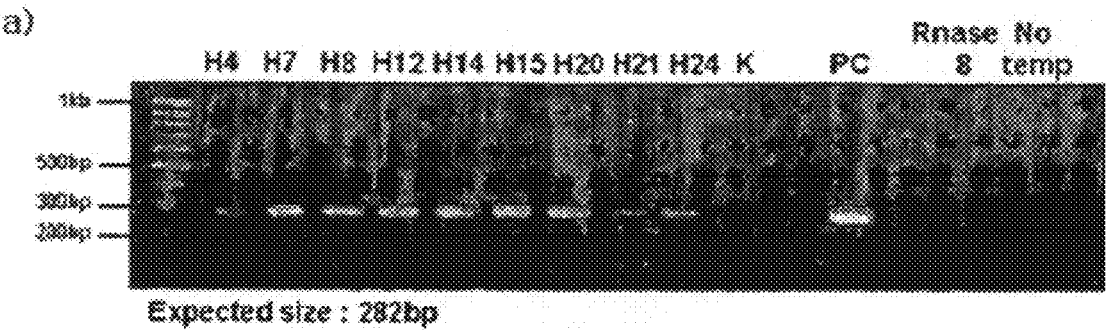
Expected size : 282bp
b)
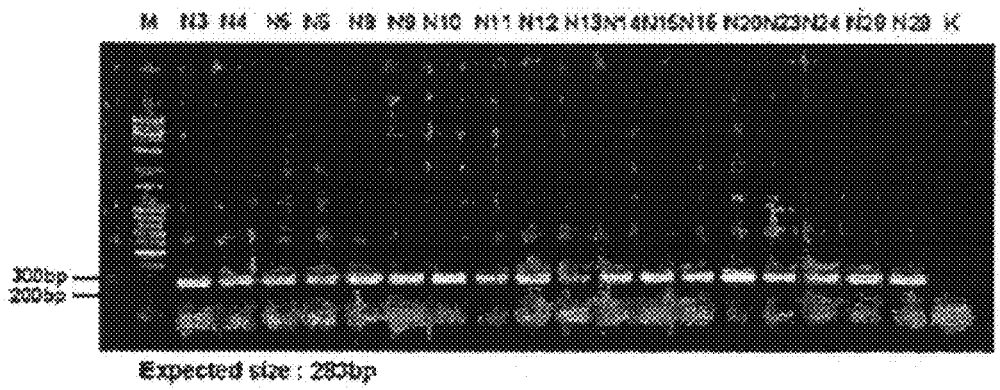
Expected size : 283bp

[Fig. 19]
a)
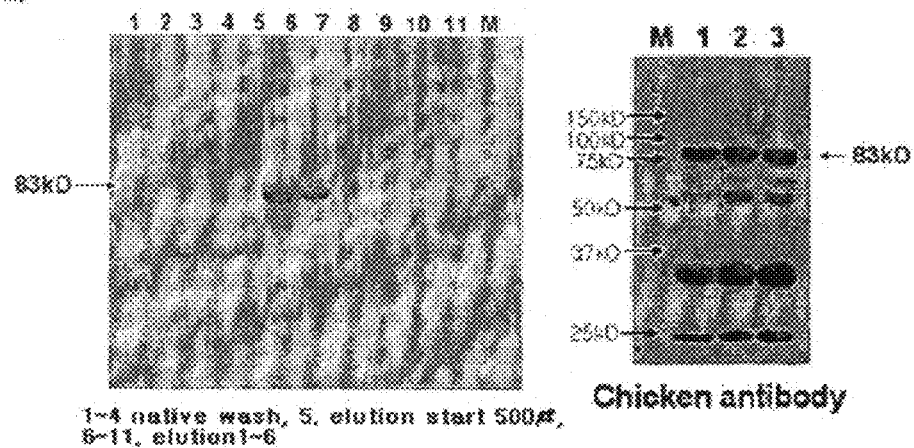
b)
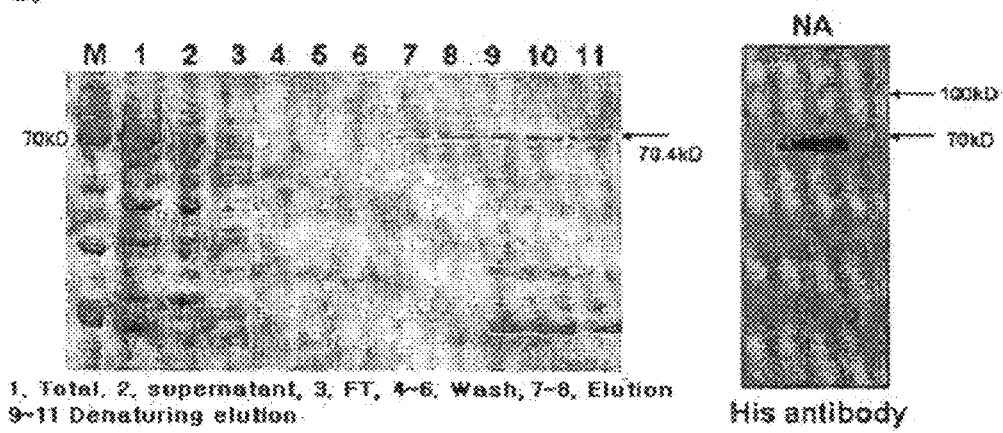
[Fig. 20]
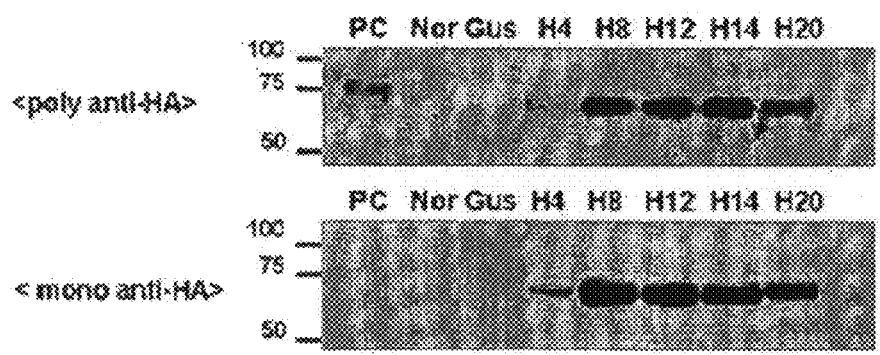

[Fig. 21]
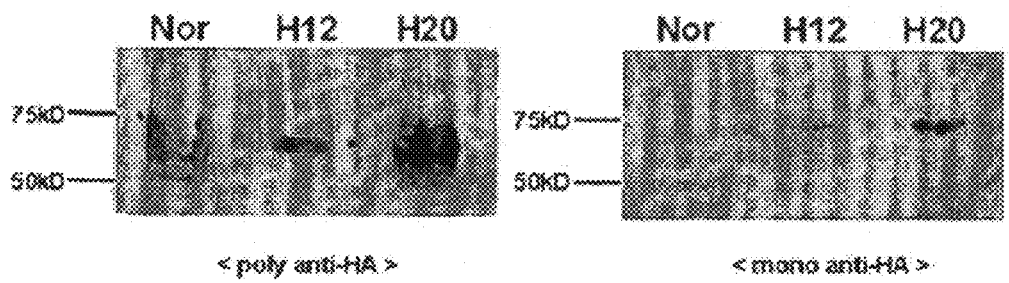
< poly anti-HA >    < mono anti-HA >
[Fig. 22]
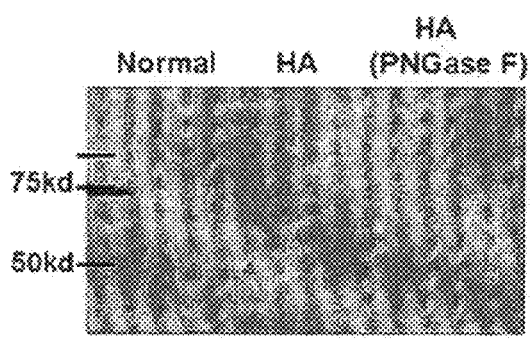
[Fig. 23]
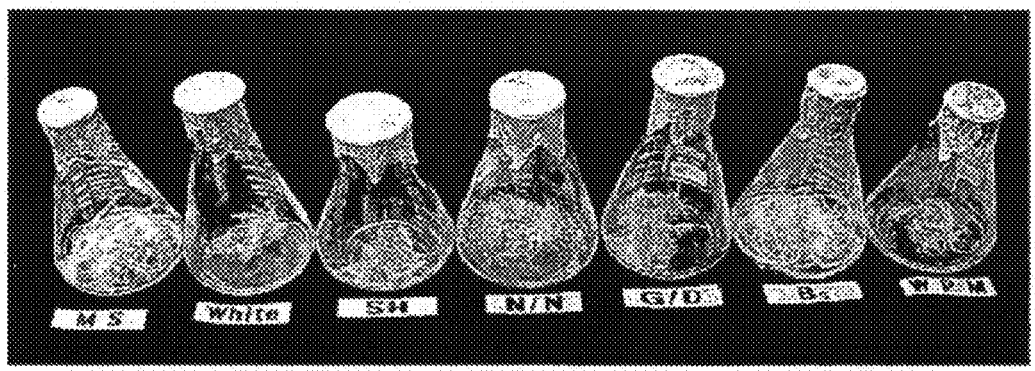
[Fig. 24]
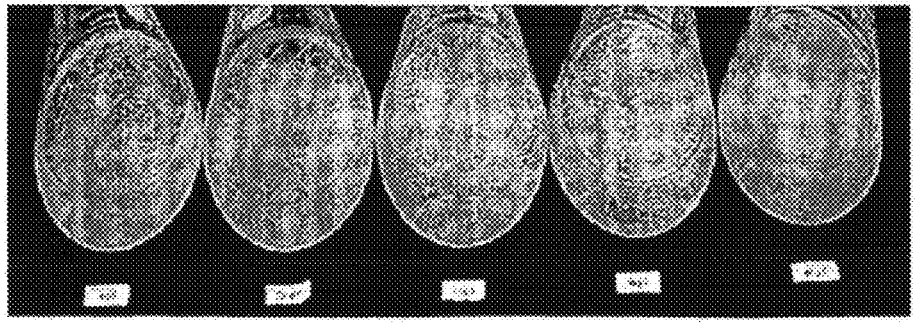

[Fig. 25]
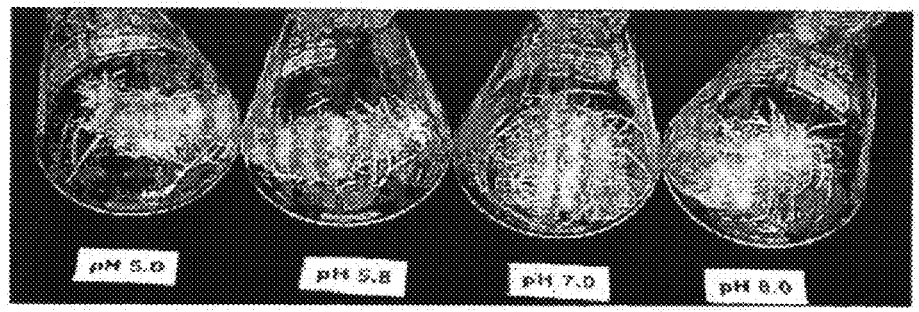
[Fig. 26]
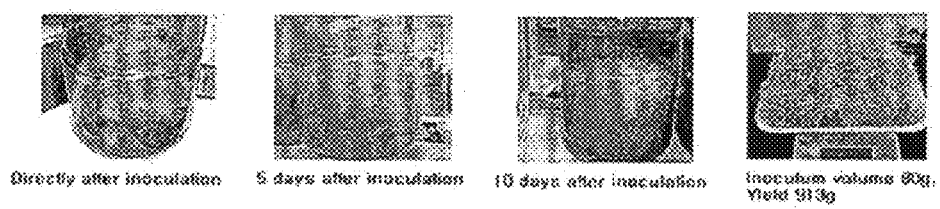
[Fig. 27]
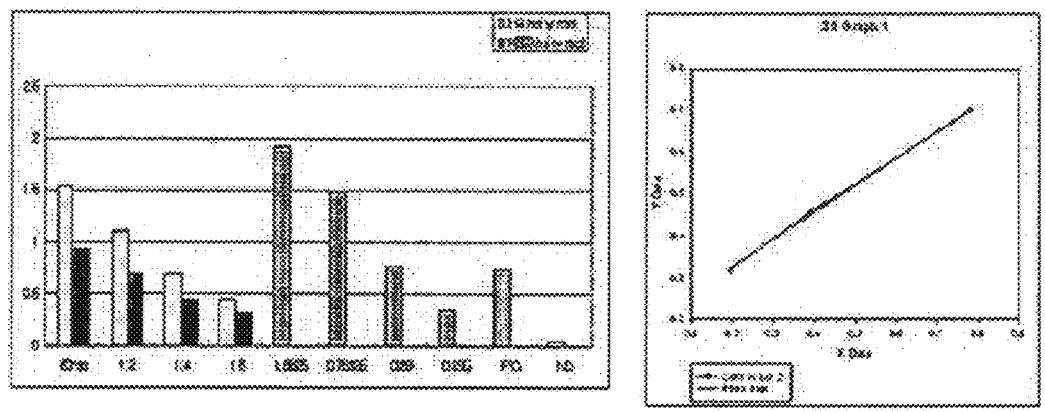

[Fig. 28]
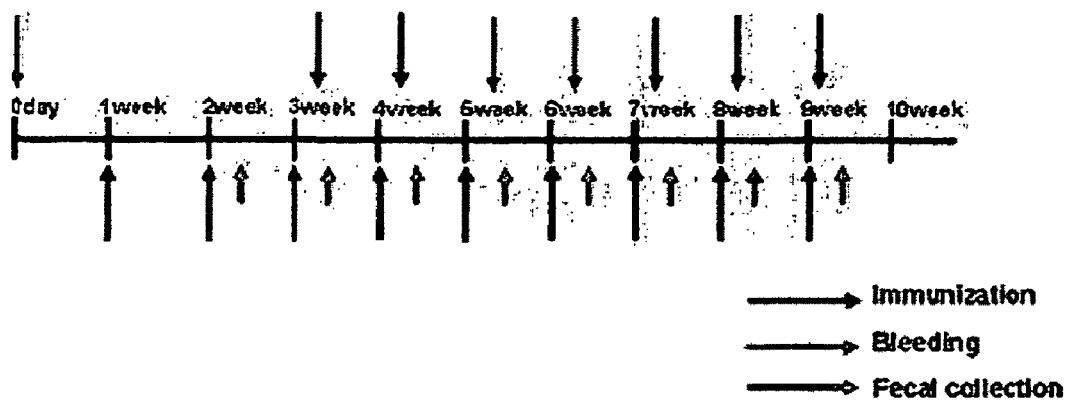
→ Immunization
→ Bleeding
⇒ Fecal collection
[Fig. 29]
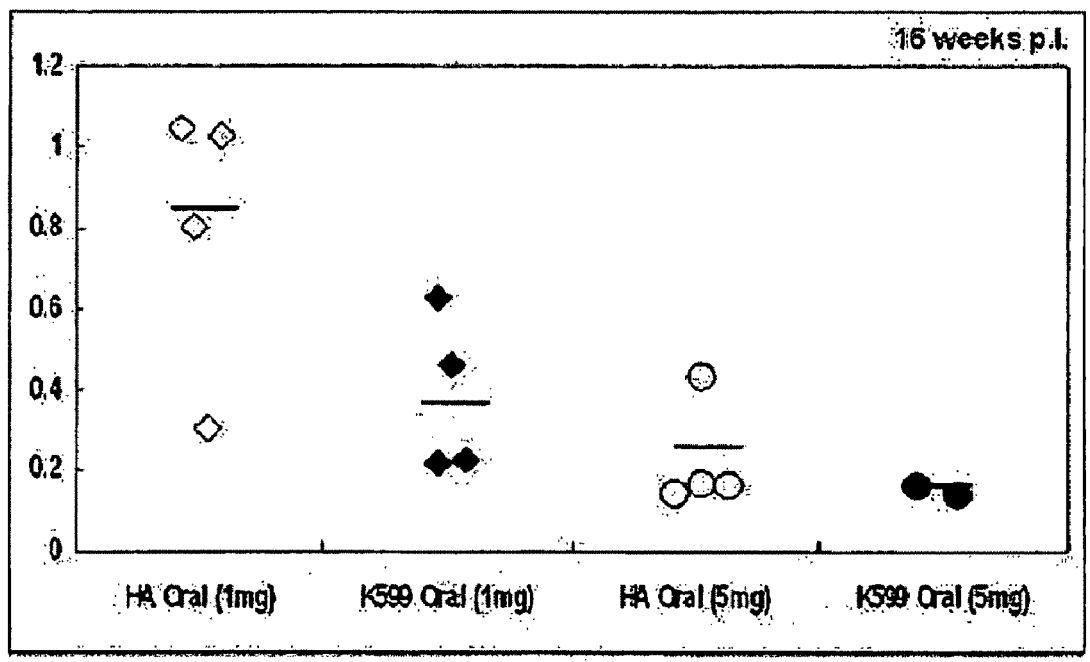

[Fig. 30]
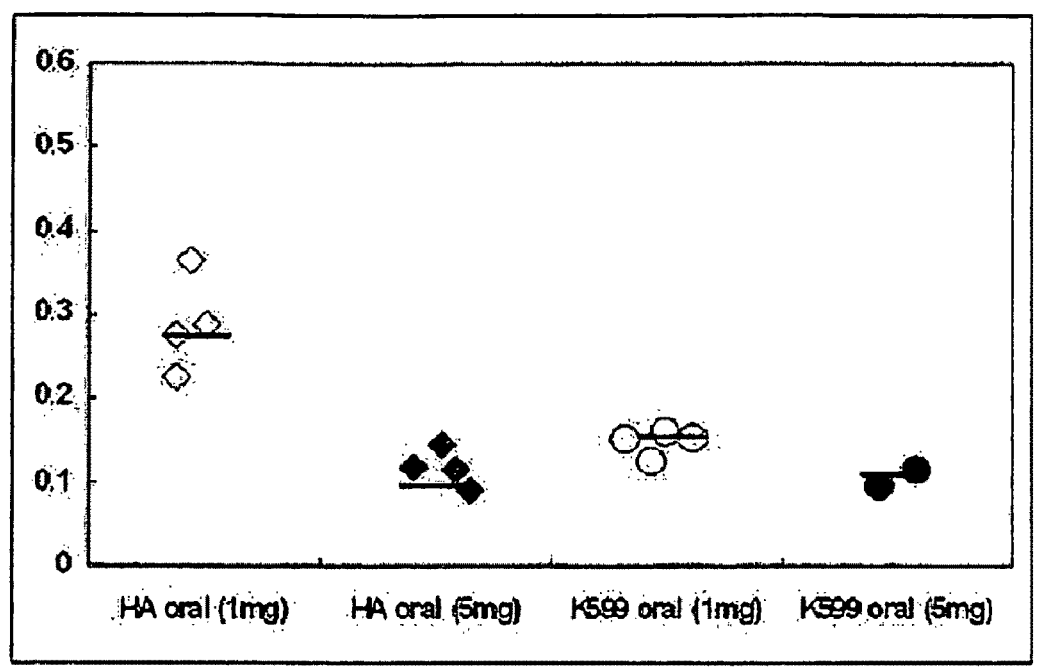

SEQUENCE LISTING

```
<160> NUMBER OF SEQ ID NOS: 41

<210> SEQ ID NO 1
<211> LENGTH: 62
<212> TYPE: DNA
<213> ORGANISM: Artificial Sequence
<220> FEATURE:
<223> OTHER INFORMATION: Synthetic primer

<400> SEQUENCE: 1
gacgcgtgag ctcggtacct cgcgaggatc ctctagagtc gacctgcagg catgcaagct      60
tg                                                                     62

<210> SEQ ID NO 2
<211> LENGTH: 34
<212> TYPE: DNA
<213> ORGANISM: Artificial Sequence
<220> FEATURE:
<223> OTHER INFORMATION: Synthetic primer

<400> SEQUENCE: 2
cggaattcag attagccttt tcaatttcag aaag                                   34

<210> SEQ ID NO 3
<211> LENGTH: 31
<212> TYPE: DNA
<213> ORGANISM: Artificial Sequence
<220> FEATURE:
<223> OTHER INFORMATION: Synthetic primer
```

-continued

```
<400> SEQUENCE: 3
cggaattcga tctagtaaca tagatgacac c                              31

<210> SEQ ID NO 4
<211> LENGTH: 36
<212> TYPE: DNA
<213> ORGANISM: Artificial Sequence
<220> FEATURE:
<223> OTHER INFORMATION: Synthetic primer

<400> SEQUENCE: 4
cgacgcgtaa ataacaaatc tcaacacaac atatac                         36

<210> SEQ ID NO 5
<211> LENGTH: 35
<212> TYPE: DNA
<213> ORGANISM: Artificial Sequence
<220> FEATURE:
<223> OTHER INFORMATION: Synthetic primer

<400> SEQUENCE: 5
cgggatccaa ataacaaatc tcaacacaac atata                          35

<210> SEQ ID NO 6
<211> LENGTH: 34
<212> TYPE: DNA
<213> ORGANISM: Artificial Sequence
<220> FEATURE:
<223> OTHER INFORMATION: Synthetic primer

<400> SEQUENCE: 6
gggtcgcgaa tggagaaaat agtgcttctt cttg                           34

<210> SEQ ID NO 7
<211> LENGTH: 35
<212> TYPE: DNA
<213> ORGANISM: Artificial Sequence
<220> FEATURE:
<223> OTHER INFORMATION: Synthetic primer

<400> SEQUENCE: 7
cccaagcttt taaatgcaaa ttctgcattg taacg                          35

<210> SEQ ID NO 8
<211> LENGTH: 35
<212> TYPE: DNA
<213> ORGANISM: Artificial Sequence
<220> FEATURE:
<223> OTHER INFORMATION: Synthetic primer

<400> SEQUENCE: 8
cggggtacca tgaatccaaa tcagaagata ataac                          35

<210> SEQ ID NO 9
<211> LENGTH: 31
<212> TYPE: DNA
<213> ORGANISM: Artificial Sequence
<220> FEATURE:
<223> OTHER INFORMATION: Synthetic primer

<400> SEQUENCE: 9
cccaagcttc tacttgtcaa tggtgaatgg c                              31

<210> SEQ ID NO 10
<211> LENGTH: 1695
<212> TYPE: DNA
```

<213> ORGANISM: Avian influenza virus
<220> FEATURE:
<221> NAME/KEY: gene
<222> LOCATION: (1)..(1695)
<223> OTHER INFORMATION: Hemaglutinin nucleotide sequence

<400> SEQUENCE: 10

```
atggagaaaa tagtacttct ttttgcaata gtcagtcttg tcaaaagtga ccagatttgc      60
attggttacc atgcaaacaa ctcgacagag caggttgaca caataatgga aaagaatgtt     120
actgtcacgc atgcccaaga catactggaa aagaaacaca atgggaagct ctgcagtcta     180
aatggagtta agcctctcat tttgagggat tgtagtgtag ctggatggct ccttggaaac     240
cccatgtgtg atgaattcct caatgtgccg gattacatag tggagaagga cagcccaatc     300
aatggcctct gctacccagg ggatttcaac gactatgaag agctgaaaca cctgttatgg     360
tcgagtagta caaaccattt tgagaaaatt caaatcattc ccaggagttc ttggtccaat     420
catgatgcct catcaggagt gagctccgca tgtccatata atgggaggtc ctcctttttc     480
agaaatgtag tgtggctcat caaaaagaac aatgcatacc caacaataaa aaggagttac     540
aataatacta accaggaaga tcttttagta ctgtggggga ttcaccatcc taatgatgca     600
gcagagcaga caaagctcta tcaaaaccca accacctatg tttctgttgg aacatcaaca     660
ctgaaccaga gatcggtccc agaaatagct accaggccca aagtaaacgg gcaaagtggg     720
agaatggagt tttctggac aatcttaaag ccaaatgatg ccatcaattt cgagagtaat      780
ggaaatttta ttgctccaga atatgcatac aaaattgtca agaaaggaga ctcaacaatc     840
atgaaaagtg gattggagta tggtaactgc aacaccaagt gtcaaactcc aatgggtgca     900
ataaactcca gcatgccatt tcacaacata caccctctca ccattgggga atgccccaaa     960
tacgtgaagt cagataggtt agtccttgca acagggctca ggaatgtccc tcaaagagaa    1020
acaagaggac tatttggggc tatagcaggc ttcatagaag gaggatggca aggaatggta    1080
gacggttggt atgggtacca ccatagcaac gagcaaggga gtggatatgc tgcagacaaa    1140
gagtccactc aaaaggcaat agatggaatc actaataagg tcaactcaat cattgacaaa    1200
atgaacactc agtttgaggc cgatggaaag gaatttaata acttagaaag gaggatagag    1260
aatttgaaca agaaaatgga agacggattc ctagatgtct ggacttataa tgctgaactt    1320
ctggttctca tggaaaatga gagaatccta gactttcatg actcaaatgt caagaacctt    1380
tatgacaagg ttcgactaca gcttagggat aatgcaaagg agctgggtaa tggttgtttc    1440
gagttctatc acaaatgtga tgatgaatgt atggaaagtg taagaaacgg aacgtatgac    1500
tacccgcagt attcagaaga ggcaagacta aacagagagg aaataagtgg agtaaaattg    1560
gaatcaatag gaacttacca aatattgtca atttattcaa cagtggcgag ttccttagca    1620
ctggcaatca tggtagctgg tctatctttc tggatgtgct ccaatggatc attgcaatgc    1680
agaatttgca tttaa                                                     1695
```

<210> SEQ ID NO 11
<211> LENGTH: 449
<212> TYPE: PRT
<213> ORGANISM: Avian influenza virus
<220> FEATURE:
<221> NAME/KEY: PEPTIDE
<222> LOCATION: (1)..(449)
<223> OTHER INFORMATION: Neuraminidase amino acid sequence

<400> SEQUENCE: 11

```
Met Asn Pro Asn Gly Lys Ile Ile Thr Ile Gly Ser Ile Cys Met Val
1               5                   10                  15
```

Ile Gly Ile Ile Val Ser Leu Met Leu Gln Val Gly Asn Met Ile Ser
                20                  25                  30

Ile Trp Val Ser His Ser Ile Gln Thr Gly Asn Gln Arg Lys Ala Glu
                35                  40                  45

Pro Ile Ser Asn Thr Lys Phe Leu Thr Glu Lys Ala Thr Ser Val Thr
 50                  55                  60

Leu Ala Gly Asn Ser Ser Leu Cys Pro Ile Ser Gly Trp Ala Val His
 65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
                100                 105                 110

Phe Leu Thr Gln Gly Ala Leu Leu Asn Asp Lys His Asn Gly Thr Val
                115                 120                 125

Lys Asp Arg Ser Pro His Arg Thr Leu Met Ser Cys Pro Val Gly Glu
130                 135                 140

Ala Pro Ser Pro Tyr Asn Ser Arg Phe Glu Ser Val Ala Trp Ser Ala
145                 150                 155                 160

Ser Ala Cys His Asp Gly Thr Ser Trp Leu Thr Ile Gly Ile Ser Gly
                165                 170                 175

Pro Asp Asn Gly Ala Val Ala Val Leu Lys Tyr Asn Gly Ile Ile Thr
                180                 185                 190

Asp Thr Ile Lys Ser Trp Arg Asn Asn Ile Leu Arg Thr Gln Glu Ser
                195                 200                 205

Glu Cys Ala Cys Val Asn Gly Ser Cys Phe Thr Val Met Thr Asp Gly
                210                 215                 220

Pro Ser Asn Gly Gln Ala Ser Tyr Lys Ile Phe Lys Met Glu Lys Gly
225                 230                 235                 240

Lys Val Val Lys Ser Val Glu Leu Asp Ala Pro Asn Tyr His Tyr Glu
                245                 250                 255

Glu Cys Ser Cys Tyr Pro Asp Ala Gly Glu Ile Thr Cys Val Cys Arg
                260                 265                 270

Asp Asn Trp His Gly Ser Asn Arg Pro Trp Val Ser Phe Asn Gln Asn
                275                 280                 285

Leu Glu Tyr Gln Ile Gly Tyr Ile Cys Ser Gly Val Phe Gly Asp Asn
                290                 295                 300

Pro Arg Pro Asn Asp Gly Thr Gly Ser Cys Gly Pro Val Ser Pro Asn
305                 310                 315                 320

Gly Ala Tyr Gly Val Lys Gly Ile Phe Ser Phe Lys Tyr Gly Asn Gly
                325                 330                 335

Val Trp Ile Gly Arg Thr Lys Ser Thr Asn Ser Arg Ser Gly Phe Glu
                340                 345                 350

Met Ile Trp Asp Pro Asn Gly Trp Thr Gly Thr Asp Ser Ser Phe Ser
                355                 360                 365

Ala Lys Gln Asp Ile Val Ala Ile Thr Asp Trp Ser Gly Tyr Ser Gly
                370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
                420                 425                 430

Val Gly Trp Ser Trp Pro Asp Gly Ala Glu Leu Pro Phe Thr Ile Asp

Lys

<210> SEQ ID NO 12
<211> LENGTH: 1262
<212> TYPE: DNA
<213> ORGANISM: Avian influenza virus
<220> FEATURE:
<221> NAME/KEY: gene
<222> LOCATION: (1)..(1262)
<223> OTHER INFORMATION: Neuaminidase nucleotide sequence

<400> SEQUENCE: 12

```
atctcaatat gggtcagtca ttcaattcag acagggaatc aacgcaaagc tgaaccaatc      60
agcaatacta aatttcttac tgagaaagct gtgacttcag taacattagc gggcaattca     120
tctctttgcc ccattagcgg atgggctgta cacagtaagg acaacagtat aaggatcggt     180
tccaaggggg atgtgtttgt tataagagag ccgttcatct catgctccca cttggaatgc     240
agaactttct ttttgactca gggagccttg ctgaatgaca agcactccaa tgggactgtc     300
aaagacagaa gccctcatag aacattaatg agttgtcctg tgggtgaggc tcccctccca     360
tataactcaa ggttttgagtc tgttgcttgg tcagcaagtg cttgccatga tggcaccagt     420
tggttgacaa ttggaatttc tggcccagac aatggggctg tggctgtatt gaaatataat     480
ggcataataa cagacactat caagagttgg aggaacaaca tactgagaac tcaagagtct     540
gaatgtgcat gcgtaaatgg ctcttgcttt actgtaatga ctgatggacc aagtaatggg     600
caggcatcat ataagatctt caaaatggaa aaaggaaaag tggttaaatc agtcgaattg     660
gatgctccta attatcacta tgaggaatgc tcctgttatc ctgatgccgg cgaaatcaca     720
tgtgtgtgca gggataattg gcatggctca ataggccat gggtatcttt caatcaaaat     780
ttggagtatc aaataggata tatatgcagt ggggttttcg gagacaatcc acgccccaat     840
gatggaacag gtagttgtgg tccggtgtcc cctaacgggc atatggggta aaagggtttt     900
catttaaata cggcaatggt gtttggatcg ggagaaccaa agcactaat tccaggagcg      960
gctttgaaat gatttgggat ccaaatgggt ggactgaaac ggacagtagc ttttcggcga    1020
agcaagatat cgtagcaata actgattggt caggatatag cgggagtttt gtccagcatc    1080
cagaactgac aggattagat tgcataagac cttgtttctg ggttgagtta atcagagggc    1140
ggcccaagga gagcacaatt tggactagtg ggagcagcat atccttttgt ggtgtaaata    1200
gtgacactgt gggttggtct tggccagacg gtgctgagtt gccattcacc attgacaagt    1260
ag                                                                    1262
```

<210> SEQ ID NO 13
<211> LENGTH: 449
<212> TYPE: PRT
<213> ORGANISM: Avian influenza virus
<220> FEATURE:
<221> NAME/KEY: PEPTIDE
<222> LOCATION: (1)..(449)
<223> OTHER INFORMATION: Neuraminidase amino acid sequence

<400> SEQUENCE: 13

```
Met Asn Pro Asn Gln Lys Ile Ile Thr Ile Gly Ser Ile Cys Met Val
1               5                   10                  15

Ile Gly Ile Val Ser Leu Met Leu Gln Val Gly Asn Met Ile Ser Ile
                20                  25                  30

Trp Val Ser His Ser Ile Gln Thr Gly Ala Ser Gln Arg Lys Glu Pro
            35                  40                  45
```

```
Ile Ser Asn Thr Lys Phe Leu Thr Glu Lys Ala Val Thr Ser Val Thr
 50                  55                  60

Leu Ala Gly Asn Ser Ser Leu Cys Pro Ile Ser Gly Trp Ala Val His
 65                  70                  75                  80

Ser Lys Asp Asn Ser Ile Arg Ile Gly Ser Lys Gly Asp Val Phe Val
                 85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Ala Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Gly Trp Ser Trp Pro Asp Gly Ala Glu Leu Pro Phe Thr Ile Asp
        435                 440                 445

Lys

<210> SEQ ID NO 14
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ttcccaggag ttcttggtcc                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
gggaccgatc tctggttcag                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gtgcatgcgt aaatggctct                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
attgtctccg aaaaccccac                                                   20

<210> SEQ ID NO 18
<211> LENGTH: 36
<212> TYPE: DNA
<213> ORGANISM: Artificial Sequence
<220> FEATURE:
<223> OTHER INFORMATION: Synthetic primer

<400> SEQUENCE: 18
gcccccggat ccgagaaaat agtacttctt tttgcg                                 36

<210> SEQ ID NO 19
<211> LENGTH: 35
<212> TYPE: DNA
<213> ORGANISM: Artificial Sequence
<220> FEATURE:
<223> OTHER INFORMATION: Synthetic primer

<400> SEQUENCE: 19
atcgggctcg agaatgcaaa ttctgcattg caatg                                  35

<210> SEQ ID NO 20
<211> LENGTH: 32
<212> TYPE: DNA
<213> ORGANISM: Artificial Sequence
<220> FEATURE:
<223> OTHER INFORMATION: Synthetic primer

<400> SEQUENCE: 20
```

```
cggaattcat ctcaatatgg gtcagtcatt ca                                    32

<210> SEQ ID NO 21
<211> LENGTH: 49
<212> TYPE: DNA
<213> ORGANISM: Artificial Sequence
<220> FEATURE:
<223> OTHER INFORMATION: Synthetic primer

<400> SEQUENCE: 21
ccgctcgagt tagtggtggt ggtggtggtg cttgtcaatg gtgaatggc                  49

<210> SEQ ID NO 22
<211> LENGTH: 28
<212> TYPE: DNA
<213> ORGANISM: Artificial Sequence
<220> FEATURE:
<223> OTHER INFORMATION: Synthetic primer

<400> SEQUENCE: 22
tattcgtctc agggagcaaa agcagggg                                         28

<210> SEQ ID NO 23
<211> LENGTH: 35
<212> TYPE: DNA
<213> ORGANISM: Artificial Sequence
<220> FEATURE:
<223> OTHER INFORMATION: Synthetic primer

<400> SEQUENCE: 23
atatcgtctc gtattagtag aaacaagggt gtttt                                 35

<210> SEQ ID NO 24
<211> LENGTH: 1767
<212> TYPE: DNA
<213> ORGANISM: Avian influenza virus
<220> FEATURE:
<221> NAME/KEY: gene
<222> LOCATION: (1)..(1767)
<223> OTHER INFORMATION: HA gene of H5N3

<400> SEQUENCE: 24
agcaaaagca ggggtccaat ctgtcaaaat ggagaaaata gtacttcttt ttgcaatagt       60
cagtcttgtc aaaagtgacc agatttgcat tggttaccat gcaaacaact cgacagagca      120
ggttgacaca ataatggaaa agaatgttac tgtcacgcat gcccaagaca tactggaaaa      180
gaaacacaat gggaagctct gcagtctaaa tggagttaag cctctcattt tgagggattg      240
tagtgtagct ggatggctcc ttggaaaccc catgtgtgat gaattcctca atgtgccgga      300
atggtcttac atagtggaga aggacagccc aatcaatggc ctctgctacc aggggatttt      360
caacgactat gaagagctga acacctgttt gagtagtaca aaccattttg agaaaattca      420
aatcattccc aggagttctt ggtccaatca tgatgcctca tcaggagtga gctccgcatg      480
tccatataat gggaggtcct cctttttcag aaatgtagtg tggctcatca aaagaacaa       540 tgcatacca acaataaaaa ggagttacaa taatactaac caggaagatc ttttagtact       600
gtgggggatt caccatccta atgatgcagc agagcagaca aagctctatc aaacccaac       660 cacctatgtt tctgttggaa catcaacact gaaccagaga tcggtcccag aaatagctac      720
caggcccaaa gtaacgggc aaagtgggag aatggagttt ttctggacaa tcttaaagcc       780
aaatgatgcc atcaatttcg agagtaatgg aaatttattt gctccagaat atgcatacaa      840
aattgtcaag aaaggagact caacaatcat gaaaagtgga ttggagtatg gtaactgcaa      900
```

-continued

```
caccaagtgt caaactccaa tggtgcaat aaactccagc atgccatttc acaacataca      960
ccctctcacc attggggaat gcccaaata cgtgaagtca dataggttag tccttgcaac     1020
agggctcagg aatgtccctc aaagagaaac aagaggacta tttggggcta tagcaggctt     1080
catagaagga ggatggcaag gaatggtaga cggttggtat gggtaccacc atagcaacga     1140
gcaagggagt ggatatgctg cagacaaaga gtccactcaa aaggcaatag atggaatcac     1200
taataaggtc aactcaatca ttgacaaaat gaacactcag tttgaggccg atggaaagga     1260
atttaataac ttagaaagga ggatagagaa tttgaacaag aaaatggaag acggattcct     1320
agatgtctgg acttataatg ctgaacttct ggttctcatg gaaaatgaga gaatcctaga     1380 cttttcatgac tcaaatgtca agaaccttta tgacaaggtt cgactacagc ttagggataa     1440
tgcaaaggag ctgggtaatg gttgtttcga gttctatcac aaatgtgatg atgaatgtat     1500
ggaaagtgta agaaacggaa cgtatgacta cccgcagtat tcagaagagg caagactaaa     1560
cagagaggaa ataagtggag taaaattgga atcaatagga acttaccaaa tattgtcaat     1620
ttattcaaca gtggcgagtt ccttagcact ggcaatcatg gtagctggtc tatctttctg     1680
gatgtgctcc aatggatcat tgcaatgcag aatttgcatt taaacttgtg agttcagatt     1740
gtagttaaaa acacccttgt ttctact                                         1767
```

<210> SEQ ID NO 25
<211> LENGTH: 1350
<212> TYPE: DNA
<213> ORGANISM: Avian influenza virus
<220> FEATURE:
<221> NAME/KEY: gene
<222> LOCATION: (1)..(1350)
<223> OTHER INFORMATION: NA gene of H5N1

<400> SEQUENCE: 25

```
atgaatccaa atcagaagat aataaccatc ggatcaatct gtatggtaat tggaatagtt       60
agcttaatgt tacaagttgg gaacatgatc tcaatatggg tcagtcattc aattcagaca      120
gggaatcaac gcaaagctga accaatcagc aatactaaat ttcttactga gaaagctgtg      180
acttcagtaa cattagcggg caattcatct ctttgcccca ttagcggatg ggctgtacac      240
agtaaggaca acagtataag gatcggttcc aagggggatg tgtttgttat aagagagccg      300
ttcatctcat gctcccactt ggaatgcaga actttctttt tgactcaggg agccttgctg      360
aatgacaagc actccaatgg gactgtcaaa gacagaagcc ctcatagaac attaatgagt      420
tgtcctgtgg gtgaggctcc ctcccccatat aactcaaggt tgagtctgt tgcttggtca      480 gcaagtgctt gccatgatgg caccagttgg ttgacaattg gaatttctgg cccagacaat      540 gggctgtgg ctgtattgaa atataatggc ataataacag acactatcaa gagttggagg      600
aacaacatac tgagaactca agagtctgaa tgtgcatgcg taaatggctc ttgctttact      660
gtaatgactg atggaccaag taatgggcag gcatcatata agatcttcaa aatggaaaaa      720
ggaaaagtgg ttaaatcagt cgaattggat gctcctaatt atcactatga ggaatgctcc      780
tgttatcctg atgccggcga aatcacatgt gtgtgcaggg ataattggca tggctcaaat      840
aggccatggg tatcttttca tcaaaatttg gagtatcaaa taggatatat atgcagtggg      900
gttttcggag acaatccacg ccccaatgat ggaacaggta ttgtggtcc ggtgtcccct      960 aacggggcat atgggtaaa aggtttttca tttaaatacg gcaatggtgt ttggatcggg      1020
agaaccaaaa gcactaattc caggagcggc tttgaaatga tttgggatcc aaatgggtgg     1080
actggaacgg acagtagctt ttcggcgaag caagatatcg tagcaataac tgattggtca     1140
```

```
ggatatagcg ggagttttgt ccagcatcca gaactgacag gattagattg cataagacct    1200
tgtttctggg ttgagttaat cagagggcgg cccaaggaga gcacaatttg gactagtggg    1260
agcagcatat cctttgtgg tgtaaatagt gacactgtgg gttggtcttg ccagacggt      1320 gctgagttgc cattcaccat tgacaagtag                                     1350

<210> SEQ ID NO 26
<211> LENGTH: 63
<212> TYPE: DNA
<213> ORGANISM: Artificial Sequence
<220> FEATURE:
<223> OTHER INFORMATION: Synthetic vector

<400> SEQUENCE: 26
ggacgcgtga gctcggtacc tcgcgaggat cctctagagt cgacctgcag gcatgcaagc     60
ttg                                                                  63

<210> SEQ ID NO 27
<211> LENGTH: 63
<212> TYPE: DNA
<213> ORGANISM: Artificial Sequence
<220> FEATURE:
<223> OTHER INFORMATION: Synthetic vector

<400> SEQUENCE: 27
caagcttgca tgcctgcagg tcgactctag aggatcctcg cgaggtaccg agctcacgcg     60
tcc                                                                  63

<210> SEQ ID NO 28
<211> LENGTH: 364
<212> TYPE: DNA
<213> ORGANISM: Artificial Sequence
<220> FEATURE:
<223> OTHER INFORMATION: HA-Original

<400> SEQUENCE: 28
ggaaaatgag agaatcctag actttcatga ctcaaatgtc aagaaccttt atgacaaggt     60
tcgactacag cttagggata atgcaaagga gctgggtaat ggttgtttcg agttctatca    120
caaatgtgat gatgaatgta tggaaagtgt aagaaacgga acgtatgact acccgcagta    180
ttcagaagag gcaagactaa acagagagga ataagtgga gtaaaattgg aatcaatagg    240
aacttaccaa atattgtcaa tttattcaac agtggcgagt tccttagcac tggcaatcat    300
ggtagctggt ctatctttct ggatgtgctc caatggatca ttgcaatgca gaatttgcat    360
ttaa                                                                 364

<210> SEQ ID NO 29
<211> LENGTH: 317
<212> TYPE: DNA
<213> ORGANISM: Artificial Sequence
<220> FEATURE:
<223> OTHER INFORMATION: H#1R

<400> SEQUENCE: 29
gcttagggat aatgcaaagg agctgggtaa tggttgtttc gagttctatc acaaatgtga     60
tgatgaatgt atggaaagtg taagaaacgg aacgtatgac tacccgcagt attcagaaga    120
ggcaagacta aacagagagg aaataagtgg agtaaaattg gaatcaatag gaacttacca    180
aatattgtca attttattcaa cagtggcgag ttccttagca ctggcaatca tggtagctgg    240
tctatctttc tggatgtgct ccaatggatc attacaatgc agaatttgca tttaaaagct    300
```
tgcgaatttc cccgatc                                                         317

<210> SEQ ID NO 30
<211> LENGTH: 295
<212> TYPE: DNA
<213> ORGANISM: Artificial Sequence
<220> FEATURE:
<223> OTHER INFORMATION: Consensus
<220> FEATURE:
<221> NAME/KEY: misc_feature
<222> LOCATION: (274)..(274)
<223> OTHER INFORMATION: n = A or G

<400> SEQUENCE: 30
gcttagggat aatgcaaagg agctgggtaa tggttgtttc gagttctatc acaaatgtga        60
tgatgaatgt atggaaagtg taagaaacgg aacgtatgac tacccgcagt attcagaaga      120
ggcaagacta acagagagg aaataagtgg agtaaaattg gaatcaatag gaacttacca       180
aatattgtca atttattcaa cagtggcgag ttccttagca ctggcaatca tggtagctgg      240
tctatctttc tggatgtgct ccaatggatc attncaatgc agaatttgca tttaa           295

<210> SEQ ID NO 31
<211> LENGTH: 564
<212> TYPE: PRT
<213> ORGANISM: Artificial Sequence
<220> FEATURE:
<223> OTHER INFORMATION: HA original

<400> SEQUENCE: 31

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Asp Tyr Ile Val Glu Lys
                85                  90                  95

Asp Ser Pro Ile Asn Gly Leu Cys Tyr Pro Gly Asp Phe Asn Asp Tyr
            100                 105                 110

Glu Glu Leu Lys His Leu Leu Trp Ser Ser Thr Asn His Phe Glu
        115                 120                 125

Lys Ile Gln Ile Ile Pro Arg Ser Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Gly Leu Glu Tyr Gly
            275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
                355                 360                 365

Ser Asn Glu Gln Gly Ser Gly Tyr Ala Ala Asp Lys Glu Ser Thr Gln
            370                 375                 380

Lys Ala Ile Asp Gly Ile Thr Asn Lys Val Asn Ser Ile Ile Asp Lys
385                 390                 395                 400

Met Asn Thr Gln Phe Glu Ala Asp Gly Lys Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
            435                 440                 445

Ile Leu Asp Phe His Asp Ser Asn Val Lys Asn Leu Tyr Asp Lys Val
            450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asp Glu Cys Met Glu Ser Val Arg Asn
                485                 490                 495

Gly Thr Tyr Asp Tyr Pro Gln Tyr Ser Glu Glu Ala Arg Leu Asn Arg
                500                 505                 510

Glu Glu Ile Ser Gly Val Lys Leu Glu Ser Ile Gly Thr Tyr Gln Ile
            515                 520                 525

Leu Ser Thr Tyr Ser Thr Val Ala Ser Ser Leu Ala Leu Ala Ile Met
            530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 32
<211> LENGTH: 93
<212> TYPE: PRT
<213> ORGANISM: Artificial Sequence
<220> FEATURE:
<223> OTHER INFORMATION: H#1R

<400> SEQUENCE: 32

Ala Lys Glu Leu Gly Asn Gly Cys Phe Glu Phe Tyr His Lys Cys Asp
1               5                   10                  15

Asp Glu Cys Met Glu Ser Val Arg Asn Gly Thr Tyr Asp Tyr Pro Gln
            20                  25                  30

Tyr Ser Glu Glu Ala Arg Leu Asn Arg Glu Glu Ile Ser Gly Val Lys

```
            35                  40                  45
Leu Glu Ser Ile Gly Thr Tyr Gln Ile Leu Ser Thr Tyr Ser Thr Val
         50                  55                  60

Ala Ser Ser Leu Ala Leu Ala Ile Met Val Ala Gly Leu Ser Phe Trp
 65                  70                  75                  80

Met Cys Ser Asn Gly Ser Leu Gln Cys Arg Ile Cys Ile
                 85                  90

<210> SEQ ID NO 33
<211> LENGTH: 498
<212> TYPE: DNA
<213> ORGANISM: Artificial Sequence
<220> FEATURE:
<223> OTHER INFORMATION: TEV-NA-Original 23-520

<400> SEQUENCE: 33
acgcgtaaat aacaaatctc aacacaacat atacaaaaca acgaatctc aagcaatcaa      60 gcattctact tctattgcag caatttaaat catttctttt aaagcaaaag caattttctg     120
aaaattttca ccatttacga acgatagcag gtaccatgaa tccaaatcag aagataataa    180
ccatcggatc aatctgtatg gtaattggaa tagttagctt aatgttacaa gttgggaaca    240
tgatctcaat atgggtcagt cattcaattc agacagggaa tcaacgcaaa gctgaaccaa    300
tcagcaatac taaatttctt actgagaaag ctgtgacttc agtaacatta gcgggcaatt    360
catctctttg ccccattagc ggatgggctg tacacagtaa ggacaacagt ataaggatcg    420
gttccaaggg ggatgtgttt gttataagag agccgttcat ctcatgctcc cacttggaat    480
gcagaacttt cttttttga                                                 498

<210> SEQ ID NO 34
<211> LENGTH: 441
<212> TYPE: DNA
<213> ORGANISM: Artificial Sequence
<220> FEATURE:
<223> OTHER INFORMATION: N#1F

<400> SEQUENCE: 34
agagaacacg ggggactcta ggacgcgtaa ataacaaatc tcaacacaac atatacaaaa     60
caaacgaatc tcaagcaatc aagcattcta cttctattgc agcaatttaa atcatttctt    120
ttaaagcaaa agcaattttc tgaaaatttt caccatttac gaacgatagc aggtaccatg    180
aatccaaatc agaagataat aaccatcgga tcaatctgta tggtaattgg aatagttagc    240
ttaatgttac aagttgggaa catgatctca atatgggtca gtcattcaat tcagacaggg    300
aatcaacgca agctgaacc aatcagcaat actaaatttc ttactgagaa agctgtgact    360
tcagtaacat tagcgggcaa ttcatctctt tgccccatta gcggatgggc tgtacacagt    420
aaggacaaca gtataaggat c                                              441

<210> SEQ ID NO 35
<211> LENGTH: 419
<212> TYPE: DNA
<213> ORGANISM: Artificial Sequence
<220> FEATURE:
<223> OTHER INFORMATION: Consensus 23-441

<400> SEQUENCE: 35
acgcgtaaat aacaaatctc aacacaacat atacaaaaca acgaatctc aagcaatcaa      60 gcattctact tctattgcag caatttaaat catttctttt aaagcaaaag caattttctg     120
aaaattttca ccatttacga acgatagcag gtaccatgaa tccaaatcag aagataataa    180
```

```
ccatcggatc aatctgtatg gtaattggaa tagttagctt aatgttacaa gttgggaaca    240
tgatctcaat atgggtcagt cattcaattc agacagggaa tcaacgcaaa gctgaaccaa    300
tcagcaatac taaatttctt actgagaaag ctgtgacttc agtaacatta gcggcaatt     360 catctctttg ccccattagc ggatgggctg tacacagtaa ggacaacagt ataaggatc     419
```

<210> SEQ ID NO 36
<211> LENGTH: 335
<212> TYPE: DNA
<213> ORGANISM: Artificial Sequence
<220> FEATURE:
<223> OTHER INFORMATION: TEV-NA-Original 1171-1505

<400> SEQUENCE: 36

```
tcgggagaac caaaagcact aattccagga gcggctttga atgatttggg gatccaaatg     60
ggtggactgg aacggacagt agcttttcgg cgaagcaaga tatcgtagca ataactgatt    120
ggtcaggata tagcgggagt tttgtccagc atccagaact gacaggatta gattgcataa    180
gaccttgttt ctgggttgag ttaatcagag ggcggcccaa ggagagcaca atttggacta    240
gtgggagcag catatccttt tgtggtgtaa atagtgacac tgtgggttgg tcttggccag    300
acggtgctga gttgccattc accattgaca agtag                               335
```

<210> SEQ ID NO 37
<211> LENGTH: 274
<212> TYPE: DNA
<213> ORGANISM: Artificial Sequence
<220> FEATURE:
<223> OTHER INFORMATION: N#1R

<400> SEQUENCE: 37

```
tagcttttcg gcgaagcaag atatcgtagc aataactgat tggtcaggat atagcgggag     60
ttttgtccag catccagaac tgacaggatt agattgcata agaccttgtt tctgggttga    120
gttaatcaga gggcggccca aggagagcac aatttggact agtgggagca gcatatcctt    180
ttgtggtgta aatagtgaca ctgtgggttg gtcttggcca gacggtgctg agttgccatt    240
caccattgac aagtagaaga ttgcgaattt cccc                                274
```

<210> SEQ ID NO 38
<211> LENGTH: 256
<212> TYPE: DNA
<213> ORGANISM: Artificial Sequence
<220> FEATURE:
<223> OTHER INFORMATION: Consensus 1250-1505

<400> SEQUENCE: 38

```
tagcttttcg gcgaagcaag atatcgtagc aataactgat tggtcaggat atagcgggag     60
ttttgtccag catccagaac tgacaggatt agattgcata agaccttgtt tctgggttga    120
gttaatcaga gggcggccca aggagagcac aatttggact agtgggagca gcatatcctt    180
ttgtggtgta aatagtgaca ctgtgggttg gtcttggcca gacggtgctg agttgccatt    240
caccattgac aagtag                                                    256
```

<210> SEQ ID NO 39
<211> LENGTH: 449
<212> TYPE: PRT
<213> ORGANISM: Artificial Sequence
<220> FEATURE:
<223> OTHER INFORMATION: N-Original

<400> SEQUENCE: 39

```
Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln Arg Gln Ala Glu Pro
        35                  40                  45

Ile Ser Asn Thr Lys Phe Leu Thr Glu Lys Ala Val Ala Ser Val Thr
    50                  55                  60

Leu Ala Gly Asn Ser Ser Leu Cys Pro Ile Ser Gly Trp Ala Val His
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asn Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
```

-continued

```
                420                 425                 430
Val Gly Trp Ser Trp Pro Asp Gly Ala Glu Leu Pro Phe Thr Ile Asp
        435                 440                 445
Lys

<210> SEQ ID NO 40
<211> LENGTH: 78
<212> TYPE: PRT
<213> ORGANISM: Artificial Sequence
<220> FEATURE:
<223> OTHER INFORMATION: NA#1R

<400> SEQUENCE: 40

Asp Ile Val Ala Ile Thr Asp Trp Ser Gly Tyr Ser Gly Ser Phe Val
1               5                   10                  15

Gln His Pro Glu Leu Thr Gly Leu Asn Cys Ile Arg Pro Cys Phe Trp
            20                  25                  30

Val Glu Leu Ile Arg Gly Arg Pro Lys Glu Ser Thr Ile Trp Thr Ser
        35                  40                  45

Gly Ser Ser Ile Ser Phe Cys Gly Val Asn Ser Asp Thr Val Gly Trp
    50                  55                  60

Ser Trp Pro Asp Gly Ala Glu Leu Pro Phe Thr Ile Asp Lys
65                  70                  75

<210> SEQ ID NO 41
<211> LENGTH: 84
<212> TYPE: PRT
<213> ORGANISM: Artificial Sequence
<220> FEATURE:
<223> OTHER INFORMATION: NA#1F

<400> SEQUENCE: 41

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln Arg Gln Ala Glu Pro
        35                  40                  45

Ile Ser Asn Thr Lys Phe Leu Thr Glu Lys Ala Val Ala Ser Val Thr
    50                  55                  60

Leu Ala Gly Asn Ser Ser Leu Cys Pro Ile Ser Gly Trp Ala Val His
65                  70                  75                  80

Ser Lys Asp Asn
```

PLANT VECTOR PBSNB-TEV, VECTORS DERIVED THEREFROM, AND METHODS OF USE

TECHNICAL FIELD

The present invention relates to a vaccine for preventing avian influenza virus infection. More particularly, the present invention relates to an oral vaccine, in which the surface protein of avian influenza virus, hemagglutinin (HA) or neuraminidase (NA) is expressed in transgenic plants, and to a method using the same.

BACKGROUND ART

In recent years, avian influenza outbreaks have occurred worldwide and affect humans to cause severe disease conditions, thereby attracting much attention. In particular, the spread of avian influenza in the poultry industry causes devastating economic losses. Accordingly, there is an urgent need to develop a vaccine to protect birds against avian influenza.

The avian influenza virus is an RNA virus belonging to the family Orthomyxoviridae, of which the genome is split to 8 RNA segments and easily modified by recombination. The influenza virus is characterized by having multiple serotypes, and no cross protection occurs between different serotypes. Currently, the virus is largely classified into three types (A, B, and C) according to antigenic differences in the nucleoprotein and the matrix protein, and all of the animal influenza viruses belong to type A.

The influenza virus type A has two proteins, hemagglutinin (HA) and neuraminidase (NA) on its surface. Hemagglutinin (HA) has a binding site with sialic acid that is present in host bronchial epithelial cells, and enters the nucleus via receptors to produce new influenza virus particles. Neuraminidase (NA) cleaves the linkage between sialic acid and viral HA to destroy the receptors, resulting in preventing the accumulation of newly produced viral particles on the infected cell membrane.

Hemagglutinin (HA) is classified into 16 HA subtypes (H1~H16), and neuraminidase (NA) into 9 NA subtypes (N1~N9) according to the antigenic properties, which potentially allows 144 various combinations of the influenza virus type A. Among them, the subtypes H5 and H7 are known to be pathogenic to birds, and the subtypes H1, H2, and H3 are known to cause influenza in humans. It has been known that avian influenza virus does not infect any animal, other than avian and swine species. However, an H5N1 avian influenza virus was isolated from patients in Hong Kong in 1997, which confirmed the possibility of human infection by the avian influenza virus. The human infection is thought to be caused by highly pathogenic viruses, which are generated by genetic mutation of avian influenza virus and human influenza virus, when they simultaneously infect human. These highly pathogenic viruses may transmit from person to person, and the risk of pandemic is increasing. Therefore, there is a need for developing a safe vaccine for birds, which is a host for avian influenza virus.

However, the avian influenza virus has a variety of serotypes, and there is little cross-immunity among the subtypes. Thus, it is hard to prevent the infection by other serotypes. Further, since the avian influenza viruses are highly apt to undergo mutation, there is no effective vaccine for preventing the avian influenza. Currently, the most effective prevention method is washing with antiseptic agents, and parenteral vaccination with inactivated influenza virus vaccine or a recombinant fowl pox virus vaccine. However, such methods can be performed, even after being infected with avian influenza and examination of the subtype of virus. Further, these vaccines may reduce the amount of virus in feces from infected poultry, but hardly prevent the spread of the disease and also incur high cost.

As alternatives, oral vaccine and edible vaccine that are directly applied to mucous membranes are suggested, and many studies have been conducted thereon, for example, oral administration of avian influenza virus itself (John M. Crowford et al., Avian disease, (1998), 42(3):486-96)) and oral spray immunization with influenza virus. However, for the preparation of these vaccines, attenuated virus or viral proteins expressed in bacteria are used, which are different from those expressed in mammals.

Meanwhile, a plant has a eukaryotic protein synthesis pathway, in which post-translational modifications being essential for mammals occur (Cabanes-Macheteau et al., Glycobiology 9.365-372 (1999)). Thus, plants are able to produce proteins similar to those expressed in mammals. For that reason, much of the focus has been placed on the production of desired proteins using transgenic plants.

The present inventors have expressed an HA or NA protein specific to avian influenza virus in transgenic plants using their properties, and established the condition for mass-production to develop an avian influenza vaccine of plant origin, which is a safe and economical mucosal vaccine, thereby completing the present invention.

DISCLOSURE

Technical Problem

It is an object of the present invention to provide an oral vaccine for preventing avian influenza virus infection using transgenic plants.

Technical Solution

In order to develop an oral vaccine for preventing avian influenza virus infection, the present inventors have transformed each of HA and NA proteins of avian influenza virus into hairy roots of Korean melon, and developed a mass production system for producing the recombinant hairy roots as a fodder additive, thereby completing the present invention.

Advantageous Effects

The transgenic plant according to the present invention is an oral vaccine for preventing the infection of high or low pathogenic avian influenza virus by using as a fodder additive for wild birds and poultry, in which the hairy roots transformed with HA or NA of avian influenza virus are mass-produced, and the high expression of anti-HA antibody is confirmed in serum from animal treated with the transgenic hairy roots. The transgenic plant as vaccine can be produced in a large amount with a low production cost, as compared to a known vaccine, in particular, can be used as the oral vaccine to achieve excellent effects such as convenience of immunization and induction of mucosal immunity.

DESCRIPTION OF DRAWINGS

FIG. 1 is a diagram illustrating a pBSNB22101 vector for the construction of the vector for plant transformation according to the present invention;

FIG. 2 is the result of PCR for the detection of Tobacco Etch Virus (TEV) leader sequence;

FIG. 3 is the result of PCR for the detection of hemagglutinin (HA) and neuraminidase (NA), which are surface proteins of avian influenza virus;

FIG. 4 is a diagram schematically illustrating the construction process of a pBSNB-TEV vector, which is the vector for plant transformation according to the present invention;

FIG. 5 is the result of PCR for the confirmation of TEV cloning into pBSNB22101;

FIG. 6 is a diagram illustrating the HA and NA cloning into pBSNB-TEV;

FIG. 7 is the result of electrophoresis showing the size and concentration of HA and NA inserts and pBSNB22101-TEV vector before ligation;

FIG. 8 is a photograph showing the insertions of HA and NA at the positions of 1695 bp and 1350 bp, in which each of the ligated plasmid DNAs is digested with Nru I/Hind III (HA) and Kpn I/Hind III (NA), used upon ligation;

FIG. 9 shows partial base sequence comparison of a cloned HA gene and a template HA gene;

FIG. 10 shows partial amino acid sequence comparison, in which an amino acid sequence translated from the HA base sequence is aligned with the amino acid sequence of the template HA protein;

FIG. 11 shows partial base sequence comparison of a cloned NA gene and a template NA gene;

FIG. 12 shows partial amino acid sequence comparison, in which an amino acid sequence translated from the NA base sequence is aligned with the amino acid sequence of the template NA protein;

FIG. 13 is the result of PCR of clones #1~5 for the selection of transformed Agrobacteria to be used for plant transformation;

FIG. 14 is a photograph showing the HA transgenic hairy root;

FIG. 15 is the result of screening the HA transgenic hairy roots by HA Ag ELISA;

FIG. 16 is the result of PCR for the detection of HA genomic DNA from the transgenic hairy roots;

FIGS. 17 a) and b) are diagrams illustrating the location of primer sequences used for RT-PCR of HA and NA;

FIGS. 18 a) and b) are the results of RT-PCR of HA and NA, in which the amount of RNA transcript is indicated by the band strength;

FIGS. 19 a) and b) are photographs showing the production of HA and NA recombinant proteins by a BL21 strain;

FIG. 20 is the result of Western blot showing the presence of HA protein from the hairy root extract;

FIG. 21 is the result of Western blot showing the expression of HA protein in the air-dried hairy root;

FIG. 22 is the result of HA glycosylation pattern analysis using PNGase F;

FIG. 23 is a photograph showing the selection of optimal medium for mass-production of HA-20 hairy root;

FIG. 24 is a photograph showing the yield of hairy root according to pH levels;

FIG. 25 is a photograph showing the selection of optimal sucrose concentration in the predetermined pH and media;

FIG. 26 is a photograph showing the applicability of selected liquid culture conditions to an 18 L mass-production system;

FIG. 27 is the result of quantifying the expression of HA protein in the freeze-dried transgenic hairy root powder;

FIG. 28 shows an immunization schedule;

FIG. 29 is a graph showing the result of HA specific serum IgG induction in the mice that are orally administered with the HA transgenic hairy root; and FIG. 30 is a graph showing the result of HA specific fecal IgA induction in mice that are orally administered with the HA transgenic hairy root.

BEST MODE

Accordingly, the present invention is characterized in that a plant is transformed with antigen proteins of avian influenza virus, and the transgenic plant is mass-produced, thereby being used for a fodder additive as an oral vaccine for preventing avian influenza virus infection. Hereinafter, the present invention will be described in detail with reference to embodiments.

In one aspect, the present invention provides a novel recombinant expression vector, in particular, being suitable for plant transformation.

There are many known vectors for plant transformation. However, in the present invention, a novel vector for plant transformation is constructed, thereby expressing the surface proteins of avian influenza virus in plants in a high yield.

The vector for plant transformation comprises (a) a replication origin operating in plant cells, (b) a promoter promoting transcription in plant cells, (c) a polycloning site capable of introducing a structural gene sequence encoding a foreign protein, (d) a polyadenylation signal sequence that operates in plant cells to form polyadenosine at a 3' end of RNA, and further may comprise an antibiotic resistance gene as a reporter gene.

In a preferred embodiment, the vector for plant transformation comprises cauliflower mosaic virus 35S promoter and 35S terminator, and further comprises a polycloning site for introducing a sequence that encodes a foreign protein to be expressed and TEV (Tobacco etch virus) leader sequence to increase expression level. Additionally, the vector for plant transformation further comprises an antibiotic resistance gene as a reporter gene. According to the preferred embodiment of the present invention, a vector for plant transformation, pBSNB-TEV is constructed, which is shown in FIG. 4.

According to the present invention, a nucleic acid sequence encoding the antigen protein of avian influenza virus is introduced into the vector for plant transformation as described above, so as to prepare a recombinant expression vector for expressing antigen proteins of avian influenza virus in plants. The antigen protein of avian influenza virus is preferably an HA or NA protein of avian influenza virus, but is not limited thereto. In addition to HA and NA, nucleic acid molecules that encode proteins capable of inducing cellular immune response, such as nucleoprotein (NP), RNA polymerase protein PB2 (polymerase basic protein 2), and polymerase acid protein (PA), can be used for the preparation of the recombinant expression vector for expressing antigen proteins of avian influenza virus.

In the preferred embodiment of the present invention, vectors having HA and NA genes were provided by National Veterinary Research & Quarantine Service to produce recombinant HA and NA proteins of avian influenza virus as antigen proteins. Specifically, the HA gene is isolated from a low pathogenic avian influenza virus, H5N3 strain, which is disclosed in Korean Patent No. 693858, and the NA gene is isolated from a highly pathogenic avian influenza virus A/CK/Korea/ES/03[H5N1](CK/Kr/ES/03), which was first isolated in Korea in 2003. pCR2.1-HA and pCR2.1-NA vectors, which contain each fragment of the above genes, were provided by National Veterinary Research & Quarantine Service, and PCR was performed to amplify the gene fragments. The gene fragments were introduced to the above vector for plant transformation to construct a recombinant expression vector for expressing antigen proteins of avian influenza virus. The construction process of the vector is described in detail in FIG. 4 and Examples 1.1 and 1.2.

In another embodiment, the present invention provides a method for preparing an avian influenza virus vaccine of plant origin, comprising the step of transforming plants using the recombinant expression vector for expressing antigen proteins of avian influenza virus.

As mentioned above, recombinant protein expressed in plants undergoes post-translational modifications by the same processes as are found in mammalians. Further, plants can be produced in a large amount under specific conditions, thereby being used for fodder additives. Accordingly, the vaccine of the present invention is excellent in terms of efficacy, safety, economy, and convenience, thereby being industrially useful.

Examples of the plant transformation method include a method for transporting a foreign DNA to plant cells using a biological vector such as *Agrobacterium*, and a method for directly transporting a foreign DNA to plant cells as transporting DNA-coated metal microparticles to plant cells (Hansen and Wright, Trends Plant Sci. 4; 226-231, 1999). Currently, the plant transformation method using a plant pathogen, *Agrobacterium* is generally used. *Agrobacterium* has an ability to transfer T-DNA of its Ti (Tumor-inducing) or Ri (root-inducing) plasmid DNA to the genome of infected plant cells. Accordingly, the recombination of a desired gene with T-DNA is performed, and then bacteria having the recombinant are co-cultured with a plant, thereby achieving the plant transformation.

In a specific embodiment of the present invention, an *Agrobacterium rhizogenes* strain having a Ri plasmid is transformed with the recombinant expression vector for expressing antigen proteins of avian influenza virus, and then the transformed *Agrobacterium* strain is used to transform a plant, in particular, cotyledon and hypocotyl of Korean melon, so as to induce transformed hairy roots of Korean melon (see Example 2). To confirm whether the genomic DNA of the hairy root is integrated with the gene encoding HA or NA, which is a surface protein of recombinant avian influenza virus, genomic DNA PCR was performed, and the expression is measured by RT-PCR, Western blot, and ELISA using anti-HA antibody (Example 3). Further, it was confirmed that the expressed HA or NA protein was glycosylated via post-translational modification (Example 4).

In order to confirm whether the transgenic plant expressing the recombinant HA or NA protein can be used as a fodder additive, the hairy roots were subjected to air-drying, followed by oral administration to mice. Sera and feces were collected from the mice, and subjected to ELISA to determine the antibody titer. As a result, HA-specific antibodies were more highly induced than in a negative control administered with the hairy roots that were transformed with *Agrobacterium rhizogenes* strain having an empty vector (see Example 8 and FIGS. 29 and 30). Accordingly, it was found that the transgenic plant itself according to the present invention can be used as an oral vaccine for preventing avian influenza virus infection.

In still another embodiment, the present invention provides an avian influenza virus vaccine, comprising the plant transformed with the recombinant expression vector for expressing antigen proteins of avian influenza virus. In this embodiment, even though the vector was transformed into Korean melon only, and the hairy roots therefrom was confirmed to be used as an oral vaccine, the plant to be used in the present invention is not limited thereto. Namely, any plant may be used, as long as it can induce hairy roots by transformation with the recombinant expression vector for expressing antigen proteins of avian influenza virus. Examples thereof include rice (*Oryza sativa*), barley (*Hordum sativum*), wheat (*Triticum aestivum* or *Triticum vulgare*), potato (*Solanum tuberosum*), sweet potato (*Ipomoea batatas*), cucumber (*Cucumis sativus*), and Korean melon (*Cucumis melo*).

In still another embodiment, the present invention provides a method for mass-producing the transgenic plant. As mentioned above, the transgenic plant itself according to the present invention may be used as a fodder additive. In accordance with this, the transgenic plant itself can act as an oral vaccine. In order to use the transgenic plant as a vaccine, a prerequisite is to establish a method for economically and stably producing the transgenic plant in a large amount. The present inventor established the conditions for mass-production of the transgenic plant.

Specifically, the production method is a method capable of mass-producing the transgenic hairy root in a bioreactor, and the optimal conditions such as type of medium, pH, and sucrose concentration was established. It can be seen that the transgenic plant according to the present invention grows well in MS or B5 medium (see FIG. 23), and better at neutral pH from pH 7 to 8 than at a known pH 5.8 (see FIG. 24). Further, in respect to sucrose concentration as an energy source, there is no difference between 15 g/L and 30 g/L. Therefore, the concentration of 15 g/L was determined in terms of the production cost (see FIG. 25).

According to such production method, the oral vaccine against avian influenza virus can be prepared with ease and at low cost.

In still another embodiment, the present invention provides a reagent for diagnosing the infection of avian influenza virus, prepared by isolating and purifying the antigen protein of avian influenza virus from the transgenic plant.

As a primary object, the present invention tried to provide an oral vaccine, by using the plant transformed with the antigen protein of the avian influenza virus as a fodder additive. Additionally, a reagent for diagnosing the infection of avian influenza virus can be prepared by easily isolating and purifying a large amount of antigen protein from the transgenic plant. Accordingly, in still another embodiment, the present invention further provides a method for preparing a diagnostic reagent for avian influenza virus infection, comprising the step of isolating the antigen proteins of avian influenza virus from the transgenic plant. According to the present embodiment, the antigen protein of avian influenza virus is isolated and purified from the transgenic plant, and then subjected to reaction with serum from bird, human or the like, so as to detect the infection of avian influenza virus.

Hereinafter, the present invention will be described in detail with reference to Examples. However, these Examples are for the illustrative purpose only, and the invention is not intended to be limited by these Examples.

MODE FOR INVENTION

1. Construction of Vector for Plant Transformation Containing Antigen Gene 1.1 Development of Vector for Plant Transformation A vector for plant transformation, containing comprising cauliflower mosaic virus 35S promoter, polycloning site, TEV (tobacco etch virus) leader sequence, and 35S terminator, was prepared as follow.

First, pCAMBIA 2300 (CAMBIA, Australia) was digested with a restriction enzyme, Hind III and dephosphorylated with calf intestine phosphatase. Then, a pDPG165 plasmid (Kausch et al., 2001) was digested with Hind III, and ligated into the digested pCAMBIA 2300 to prepare a pBS221 plasmid. The restriction sites in the pBS221 plasmid (BamH I, Kpn I, Xba I) were digested with each restriction enzyme, and polymerization was performed with T7 polymerase, respectively.

Meanwhile, in order to insert the polycloning site into pBI221 (Clontech, USA), pBI221 was digested with Sac I and Xba I, ligated with a synthetic primer 1, oligonucleotide (SEQ ID NO. 1: 5'-GACGCGTGAGCTCGGTACCTCGC-GAGGATCCTCTAGAGTCGACCTGCAGG CATG-CAAGCTTG-3', and subjected to polymerization with T7 polymerase, followed by blunt end ligation. In pBI221 containing the oligonucleotide, a fragment containing CaMV 35 promoter, polycloning site and NOS terminator was amplified using the oligonucleotide, primer 2 (SEQ ID NO. 2: 5'-CGGAATTCAGATTAGCCTTTTCAATTTCAGAAAG-3', and primer 3 (SEQ ID NO. 3: 5'-CGGAATTCGATCTAG-TAACATAGATGACACC-3' by PCR (PCR condition: 95° C. 5 min, one cycle; 94° C. 30 sec, 60° C. 30 sec, 72° C. 2 min, 30 cycles; 72° C. 7 min, 1 cycle), followed by digestion with a restriction enzyme, EcoR I. Then, the fragment was cloned into pBS221 to prepare a pBSNB22101 vector (FIG. 1).

Further, to increase expression level, TEV (Tobacco etch virus) leader sequence was amplified using pRTL2 (Carrington and Freed et al., J. Virol. 64, 1990) as a template, a primer 4 (SEQ ID NO. 4: 5'-CGACGCGTAAATAA-CAAATCTCAACACAACATATAC-3', and a primer 5 (SEQ ID NO. 5: 5'-CGGGATCCAAATAACAAATCTCAACA-CAACATATA-3' by PCR (PCR condition: 95° C. 5 min, one cycle; 94° C. 30 sec, 60° C. 30 sec, 72° C. 1 min, 30 cycles; 72° C. 7 min, 1 cycle), followed by digestion with Mlu I and Kpn I (FIG. 2). The TEV fragment having a size of 142 bp was inserted into the restriction sites, Mlu I and Kpn I of pBSNB22101. The ligated vector was transformed into DH5α and cultured on plates with kanamycin (Km) at 37° C. Since the pBSNB22101 vector had a kanamycin resistance gene, colonies were formed on the plates. On the next day, colonies formed on plates were selected, and cultured in 3 ml of LB liquid media having kanamycin at 37° C., followed by miniprep. Enzyme digestion was performed to confirm the presence of TEV. As shown in FIG. 5, a band of 142 bp corresponding to TEV was found. The vector was designated as pBSNB-TEV, constructed as the vector for plant transformation. The entire process of constructing the vector is shown in FIG. 4.

1.2 Development of Vector for Plant Transformation Containing HA and NA Genes of Avian Influenza Virus In connection with the production of the vector for plant transformation containing HA and NA genes of avian influenza virus, vectors containing HA and NA genes were provided by National Veterinary Research & Quarantine Service, so as to produce HA and NA recombinant proteins.

The HA gene contained in the vector is a gene obtained from low pathogenic virus A/wild bird feces/Korea/CSM2/02 [H5N3](Wbf/Kr/CSM2/02), and viral RNA was extracted using an RNeasy mini kit (QIAGEN, Valencia, Calif.). The method for obtaining the HA gene is the same as in published paper (Lee, C. W., D. L. Suarez, T. M. Tumpey, H. W. Sung, Y. K. Kwon, Y. J. Lee, J. G. Choi, S. J. Joh, M. C. Kim, E. K. Lee, J. M. Park, X. Lu, J. M. Katz, E. Spackman, D. E. Swayne, and J. H. Kim. *Characterization of highly pathogenic H5N1 avian influenza A viruses isolated from South Korea. J. Virol.* 79:3692-3702. 2005.), described as follows:

The HA gene fragment of about 1.7 kb was amplified using an HA-F forward primer (SEQ ID NO. 22: 5'-TATTCGTCT-CAGGGAGCAAAAGCAGGG G-3', an HA-R reverse primer (SEQ ID NO. 23: 5'-ATATCGTCTCGTATTAGTA-GAAACAAGGGTGTTTT-3', and a One-Step RT-PCR kit (QIAGEN). RNA extraction was performed using an RNAeasy mini kit (Qiagen) and PCR was performed using a onestep RT-PCR kit (Qiagen) (PCR condition: cDNA synthesis (50° C. 30 min, 95° C. 15 min), denaturation (94° C., 45 sec), annealing (53° C., 15 sec), and extension (72° C., 1 min and 30 sec) for 30 cycles, and further reaction (72° C. for 5 min). The amplified gene fragment was subjected to sequencing analysis, and the result is the same as SEQ ID NO. 24. The amplified HA fragment was cloned into a pCR2.1 vector using a TA cloning kit (Invitrogen, N.Y., USA). The cloned vector, pCR2.1-HA was provided as a template of HA gene.

Meanwhile, the NA gene is a gene obtained from a highly pathogenic virus A/CK/Korea/ES/03[H5N1](CK/Kr/ES/03), which is first isolated in Korea in 2003, and viral RNA was extracted using an RNeasy mini kit (QIAGEN, Valencia, Calif.). As in published paper (Lee et al. J. Virol. 79:3692-3702. 2005.), the NA gene was amplified using a One-Step RT-PCR kit (QIAGEN), and then cloned into the pCR2.1 vector using a TA cloning kit (Invitrogen, N.Y., USA). The cloned vector, pCR2.1-NA was provided as a template of NA gene. Sequence information for the NA gene of CK/Kr/ES/03 strain has been deposited in GenBank (ACCESSION No. AY676043), which is represented by SEQ ID NO. 25.

To amplify the HA gene in the provided vector, pCR2.1-HA, a primer 6 (SEQ ID NO. 6:5'-GGGTCGCGAATG-GAGAAAATAGTGCTTCTTCTTG-3' and a primer 7 (SEQ ID NO. 7: 5'-CCCAAGCTTTTAAATGCAAATTCTGCAT-TGTAACG-3' were designed. The NA gene in the provided vector, pCR2.1-NA has a size of about 1350 bp, and to amplify the NA gene, a primer 8 (SEQ ID NO. 8: 5'-CGGGG-TACCATGAATCCAAATCAGAAGATAATAAC-3' and a primer 9 (SEQ ID NO. 9: 5'-CCCAAGCTTCTACTTGT-CAATGGTGAATGGC-3' were prepared.

The genes coding for HA and NA were amplified using the primers by PCR (condition: 95° C. 5 min, 1 cycle; 94° C. 30 sec, 60° C. 30 sec, 72° C. 1 min, 40 cycles; 72° C. 7 min, 1 cycle), and the PCR product was subjected to electrophoresis. As a result, bands of 1695 bp and 1350 bp corresponding to HA gene and NA gene were found (FIG. 3).

Next, to ligate each of the amplified HA and NA genes into the vector for plant transformation, pBSNB-TEV prepared in Example 1.1, the amplified HA gene was digested with Nru I and Hind III, and the amplified NA gene was digested with Kpn I and Hind III (FIG. 6). Before ligation, the size of the insert and vector and their concentrations were determined by agarose gel electrophoresis (FIG. 7). The vector and insert were ligated in a ratio of 1:3 at 16° C. for 30 minutes. Two ligated plasmids were transformed into DH5α by heat shock at 42° C., and then cultured on kanamycin plates at 37° C. The next day, the selected colonies were cultured in 3 ml of LB media at 37° C. overnight. After performing miniprep, the obtained plasmid DNAs were digested with Nru I/Hind III (HA) and Kpn I/Hind III (NA) to confirm the insertions of HA and NA.

Inserts of 1695 bp and 1350 bp corresponding to HA and NA genes were found in each DNA obtained from four clones by miniprep. Among them, each of clone NO. 1 (#1) was selected, and then restriction enzyme analysis was performed to confirm whether the inserted DNAs are HA and NA genes (FIG. 8). Further, sequencing analysis was performed to confirm whether the base sequences of cloned HA and NA (SEQ ID NOs. 10 and 12) correspond to the base sequences of template HA and NA. It was also confirmed that amino acid sequences (SEQ ID NOs. 11 and 13) translated from the base sequences are correct (see FIGS. 9 to 12).

Accordingly, the vector for plant transformation, pBSNB-TEV cloned with HA gene is designated as pBSNB-TEV-HA#1-1, and the vector for plant transformation, pBSNB-TEV cloned with NA gene is designated as pBSNB-TEV-NA#1-1.

1.3 Preparation of *Agrobacterium* Transformant for Plant Transformation pBSNB-TEV-HA#1-1 and NA#1-1 prepared in Example 1.2 were transformed into an *Agrobacterium rhizogenes* strain, K599 by a freeze-thaw method (Glevin et al., Plant molecular biology. Kluwer academic Publishers A3/7, 1988).

First, competent K599 cells were prepared, and mixed with the vectors. The heat shock was applied at 37° C. for 5 min. Then, 1 ml of antibiotic-free YEP media (10 g/L yeast, 5 g/L NaCL, and 10 g/L peptone) was added thereto, and cultured at 28° C. for 4 hrs. Subsequently, the cells were cultured on YEP plates (10 g/L yeast, 5 g/L NaCL, 10 g/L peptone, 15 g/L agar) containing kanamycin (Km)(100 ug/ml) at 28° C. for 2 days. Colonies were selected from the plates, and cultured in 3 ml of YEP media at 28° C. Genomic DNA was extracted from the transformed K599, and PCR was performed to confirm the integration into genomic DNA. PCR was performed at an annealing temperature of 60° C. for 35 cycles. Then, the product was subjected to agarose gel electrophoresis to confirm each band. As shown in FIG. 13, each band of 1695 bp and 1350 bp corresponding to HA and NA was found. Agrobacteria transformed with each clone NO. 1 (#1) of HA and NA were selected to use for plant transformation.

2. Transformation of Inserted HA and NA Genes into Hairy Root

The Agrobacteria K599 transformed with HA and NA, prepared in Example 1.3, were transformed into cotyledon and hypocotyls of Korean melon. The sterilized seeds of Korean melon were sown and germinated for 4 days under sterile conditions. Then, the stalks were removed from 4-day-old seeds and the young leaves were wounded. These wounded leaves were transformed with *Agrobacterium rhizogenes* strain, K599, which was transformed with pBSNB-TEV-HA#1-1 and NA#1-1 plasmids.

Each transformed K599 strain with HA and NA was cultured in 30 ml of YEP media containing kanamycin (Km) (100 ug/ml) at 28° C., and then centrifuged at 4,000 rpm for 15 min to discard supernatant. The pellets were resuspended with 30 ml of dilution of selection media (pH 5.8) containing Murashige-Skoog (MS0) media (with vitamin) (Duchefa, Netherlands), 3.0% sucrose, 1 mg/l BA (benzyladenine), 0.1 mg/l NAA (napthalene acidic acid), 0.3% phytase, 300 mg/l kanamycin and 500 mg/l carbenicillin, and sterilized water (1:2). Optical density (O.D.) values were measured, and dilution was performed with 50% MS0 to give the total OD value of 0.4. The wounded leaves of Korean melon were mixed with the above prepared solution for 15 min. Water was completely removed from the leaves using sterilized 3M paper. Then, the leaves were transferred to MS0 plates, cultured at 22° C. for 2 days in the dark, and then transferred to selection media, MS (Carbenicillin500, KM300).

The media were observed every day to discard the leaves infected with *Agrobacterium rhizogenes*, and other leaves in the same media were transferred to fresh selection media until hairy roots were induced. After 1~2 weeks, the formation of hairy root was observed. One root of them was cut, and cultured in MS media containing kanamycin to select the transferred gene and carbenicillin to prevent the overgrowth of *Agrobacterium rhizogenes*. As shown FIG. 14, the hairy roots transformed with HA were obtained, and in the same manner, the hairy roots transformed with NA were obtained. Further, as a negative control, a transgenic plant K599 transformed with a K599 strain, which was not transformed with the plasmids, was obtained. The compositions of the MS0, MS0 and MS media are shown in the following Table 1.

TABLE 1

| MS0 | % MS medium (with Vitamin) 30 g/l sucrose, pH 5.8 |
|---|---|
| MS0 plate | % MS medium (with Vitamin) 30 g/l sucrose, pH 5.8 0.3% agar |
| MS (Cb500, Km300) plate | % MS medium (with Vitamin) 30 g/l sucrose, pH 5.8 0.3% agar Cabenicillin 500 ug/ml Kanamycin 300 ug/ml |

3. Confirmation of Antigenic HA Protein Expression in Transgenic Hairy Root 3.1 HA Ag ELISA In order to confirm the HA expression in 30 transgenic hairy root lines and compare the expression level between the lines, ELISA was performed using HA antibody. First, each hairy root was collected from media, and the agar ingredient was removed from the hairy root. The hairy root was ground into a fine powder with liquid nitrogen in a mortar and pestle. A lysis buffer (50 mM Tris-HCl, 400 mM NaCl, 1 mM EDTA, 5% glycerol, 1% Triton X-100, pH 7.5) containing a general protease inhibitor (Sigma, ST. LOUIS, USA) was added to the hairy root powder, and the protein was extracted by centrifuge at 4° C. Then, the concentration of the total extract was determined by a Bradford assay. 60 µg of the total extract was diluted with the lysis buffer to a total volume of 110 µl, and then loaded on the plate coated with monoclonal anti-HA antibody. After incubation at 37° C. for 1 hr, the plate was washed with a washing buffer 5 times. Then, monoclonal anti-HA-HRP was added thereto, and incubated at 37° C. for 30 min. After washing with the washing buffer 5 times, the substrate was added, and color-developed. After 10 min, a blocking solution was added to block the reaction, and absorbance was measured at 450 nm using a dual beam spectrophotometer. The expression levels in 30 transgenic hairy root lines were different from each other, and the cut-off level was set at the OD value of 0.3. The samples having the OD values of 0.3 or more were selected (FIG. 15).

3.2 HA Genomic DNA PCR

If the HA gene is located in the T DNA region of the transformed *Agrobacterium rhizogenes*, the HA gene would be integrated into the chromosome of the transgenic plant. Therefore, genomic DNA PCR was performed to confirm the presence of HA gene in transgenic hairy roots having higher OD value, obtained from the result of HA Ag ELISA. The HA primer set prepared in the first cloning step was used to perform general PCR. A HA band of 1,695 bp was found in the HA transgenic hairy root. Consequently, it can be seen that the HA gene was integrated into the chromosome of the hairy root (FIG. 16).

3.3 RT-PCR Analysis of HA and NA Transgenic Hairy Roots

An RT-PCR analysis was performed to confirm transcription of HA and NA genes in the transformants. As shown in FIG. 17a, a specific primer set was designed. RNA was extracted using a Trireagent from the plant having higher OD value, obtained from the result of HA Ag ELISA, and cDNA was prepared. Then, PCR was performed using the primer set to amplify the 398~680 region of HA1 (SEQ ID NOs. 14 and 15) at 52° C. for 35 cycles. Further, the RT-PCR analysis was performed to confirm the transcription of NA gene in the transformant. As shown in FIG. 17b, a specific primer set (SEQ ID NOs. 16 and 17) was constructed. RNA was extracted from NA transgenic hairy root, and cDNA was prepared. Then, PCR was performed using the primer to amplify the 398~680 region of NA (SEQ ID NOs. 16 and 17) at 52° C. for 35 cycles.

As shown FIG. 18a, specific bands corresponding to 282 bp were detected in all of the HA transformants, and no band was observed in the empty transformant. It can be seen that the band strength depends on the amount of message. As shown FIG. 18b, specific bands corresponding to 282 bp were detected in all of the NA transformants, and no band was observed in the hairy root infected with bacterium, which was not transformed. It can be seen that the band strength depends on the amount of message.

3.4 Production of HA and NA Antibodies in Rabbit

To produce antibodies used for the detection of HA and NA expression in Western blot and ELISA, a bacterial expression system was used to express HA and NA proteins. First, the sets of primers were constructed for cloning (see SEQ ID NOs. 18 to 21). HA was cloned into pET32a, NA into pGEX-GST4T-1, and expressed in BL21(DE3). The expression of HA and NA was detected at 83 kDa and 70 kDa, respectively. The expression condition was at an IPTG concentration of 0.5~1 mM and a temperature of 37° C. for 3 hrs.

In order to confirm whether the expressed proteins were HA and NA, Western blot was performed using sera from chickens infected with avian influenza for the detection of HA expression, and using His antibody for the detection of NA expression. The pET vector has His-tags at both ends. Thus, HA was purified using an Ni-NTA agarose (Quiagen, Valencia, USA) (FIG. 19a). NA was also purified using the Ni-NTA agarose by adding His sequence to the primer sequence (FIG. 19b). Each of two rabbits was immunized with 23.5 μg for 10 weeks, and sera were collected from the rabbits. The collected sera were used for Western blot to determine the HA protein that was expressed in the transgenic plant (see FIGS. 20 and 21).

3.5 Western Blot for HA Protein Expression

Western blot was performed to confirm the correlation between expression levels of transcripts and proteins. As a positive control, the HA protein expressed in bacteria was used, and determined using polyclonal anti-HA antibody and monoclonal anti-HA antibody. Samples were prepared in the same manner as in the Ag ELISA. 52 μg of protein was loaded onto 10% SDS-PAGE gel, and run to a stacking gel at 100 V using a Tris-glycine buffer. Then, a resolving gel was subjected to electrophoresis at 200 V. The separated proteins were transferred to a PVDF membrane using a Mini-Trans-Blot electrophoretic transfer cell (Bio-rad, Hercules, USA) at 100 V for 1 hr. The membrane was blocked using 5% skim milk-TBST (TBS buffer plus 0.05% tween 20) at room normal temperature for 3 hrs, and slightly washed with 0.05% TBST. Then, the membrane was incubated with rabbit polyclonal anti-HA antibody (poly HA Ab) or mouse monoclonal anti-HA antibody at 1:4,000 dilution (2% skim milk in 0.2% TBST) and 1:2,000 dilution (2% skim milk in 0.2% TBST) at 4° C. overnight. Then, after washing for 15 min three times, the membrane was probed with horseradish peroxidase (HRP) conjugated rabbit anti-mouse-IgG or HRP-conjugated goat anti-rabbit IgG at a dilution of 1:2,000 (2% skim milk in 0.2% TBST) and 1:10,000 (2% skim milk in 0.2% TBST) at room temperature for 2 hrs. The membrane was washed with 0.05% TBST for 15 min three times, and then visualized using an ECL solution.

The hairy root transformed with HA gene was found to have a specific band, which was not detected in transformant with mock DNA. The result was the same as results of using other different types of antibodies (FIG. 20). The expression level in each lane was unique, which is similar pattern to the result of RT-PCR. Namely, the transformant HA12, HA8, and HA20 were found to show higher expression levels of HA protein. In order to determine immunoactivity by an animal test, the transformant HA12, HA8, and HA20 were freeze-dried and ground into powder. Western blot was performed to confirm the expression of HA protein in the powder. In the case of using polyclonal anti-HA antibody and monoclonal anti-HA antibody, the specific bands were detected in all of the samples. The transformant H20 showed higher expression level than HA20, thereby being used for the animal test (FIG. 21).

4. Glycosylation Pattern Analysis

In the Western blot, the specific band was always found to have a bigger size than the expected size of 63.5 kD, which was confirmed by glycosylation pattern analysis. 20 μg of protein was subjected to deglycosylation using PNGase F (New England BioLabs, Beverly, USA), and subjected to Western blot using polyclonal anti-HA antibody. As a result, the band size was found to be the same as the expected size (FIG. 22).

5. Establishment of Liquid Culture Condition for Mass-Production of Hairy Root

From the result of Western blot analysis in Example 3.5, it can be seen that the air-dried transgenic hairy root, H20 showed higher expression level of HA protein. Accordingly, for the mass-production of hairy root H20, the optimization of liquid culture condition was performed.

5.1 Selection of Optimal Medium for Mass-Production of Hairy Root HA-20

In order to select optimal media among MS (Murashige-Skoog) and B5, SH (Schenk-Hildebrandt), G/D, N/N, WPM and White media, which are used for tissue culture in the mass-production system, 20 ml of each media was put into a 300 ml flask, and 0.8 g of hairy root H20 was inoculated and cultured for 10 days. As shown in FIG. 23, the hairy root was found to be produced in MS and B5 media in a high yield. The composition of each medium is shown in the following Table 2.

TABLE 2

| Medium | Ingredients | mg/L |
|---|---|---|
| Gamborg's B-5 basal salt mixture | Ammonium sulfate | 134 |
| | Boric acid | 3 |
| | Calcium chloride anhydrous | 113.24 |
| | Cobalt chloride 6H$_2$O | 0.025 |
| | Cupric sulfate 5H$_2$O | 0.025 |
| | Na2-EDTA | 37.3 |
| | Ferrous sulfate 7H$_2$O | 27.8 |
| | Magnesium sulfate | 122.09 |
| | Manganese sulfate H$_2$O | 10 |
| | Molybdic acid (sodium salt) 2H$_2$O | 0.25 |
| | Potassium iodide | 0.75 |

TABLE 2-continued

| Medium | Ingredients | mg/L |
|---|---|---|
| | Potassium nitrate | 2500 |
| | Sodium phosphate monobasic | 130.5 |
| | Zinc sulfate 7H$_2$O | 2 |
| Schenk and Hildebrandt(SH) Basal Salt Mixture | Ammonium phosphate monobasic | 300 |
| | Boric acid | 5 |
| | Calcium chloride anhydrous | 151 |
| | Cobalt chloride 6H$_2$O | 0.1 |
| | Cupric sulfate 5H$_2$O | 0.2 |
| | Na2-EDTA | 20 |
| | Ferrous sulfate 7H$_2$O | 15 |
| | Magnesium sulfate | 195.4 |
| | Manganese sulfate H$_2$O | 10 |
| | Molybdic acid (sodium salt) 2H$_2$O | 0.1 |
| | Potassium iodide | 1 |
| | Potassium nitrate | 2500 |
| | Zinc sulfate 7H$_2$O | 1 |
| McCown's Woody Plant(WP) Basal Salt Mixture | Ammonium nitrate | 400 |
| | Boric acid | 6.2 |
| | Calcium chloride anhydrous Boric acid | 72.5 |
| | Calcium nitrate | 386 |
| | Cupric sulfate 5H$_2$O | 0.25 |
| | Na2-EDTA | 37.3 |
| | Magnesium sulfate | 180.7 |
| | Manganese sulfate H$_2$O | 22.3 |
| | Molybdic acid (sodium salt) 2H$_2$O | 0.25 |
| | Potassium phosphate monobasic | 170 |
| | Potassium sulfate | 990 |
| | Zinc sulfate 7H$_2$O | 8.6 |
| White's basal salt mixture | Boric acid | 1.5 |
| | Calcium nitrate | 200 |
| | Ferric sulfate | 2.5 |
| | Magnesium sulfate | 360 |
| | Manganese sulfate H$_2$O | 5.04 |
| | Potassium chloride | 65 |
| | Potassium iodide | 0.75 |
| | Potassium nitrate | 80 |
| | Sodium phosphate monobasic | 16.5 |
| | Sodium sulfate | 200 |
| | Zinc sulfate | 2.67 |
| GRESSHOFF & DOY BASAL MEDIUM | Ammonium Nitrate | 1000 |
| | Boric Acid | 0.3 |
| | Calcium Nitrate | 241.2 |
| | Cobalt Chloride•6H$_2$O | 0.025 |
| | Cupric Sulfate•5H$_2$O | 0.025 |
| | Na2 EDTA•2H$_2$O | 37.25 |
| | Ferrous Sulfate•7H$_2$O | 27.85 |
| | Magnesium Sulfate, Anhydrous | 17.099 |
| | Manganese Sulfate•H$_2$O | 1 |
| | Molybdic Acid (Sodium Salt)•2H$_2$O | 0.025 |
| | Potassium Chloride | 65 |
| | Potassium Iodide | 0.8 |
| | Potassium Nitrate | 1000 |
| | Potassium Phosphate, Monobasic | 300 |
| | Zinc Sulfate•7H$_2$O | 0.3 |
| | D-Biotin | 0.2 |
| | Glycine (Free Base) | 4 |
| | myo-Inositol | 10 |
| | Nicotinic Acid (Free Acid) | 0.1 |
| | Pyridoxine•HCl | 0.1 |
| | Thiamine•HCl | 1 |
| NITSCH & NITSCH BASAL MEDIUM w/VITAMINS | Ammonium Nitrate | 720 |
| | Boric Acid | 10 |
| | Calcium Chloride, Anhydrous | 166 |
| | Cupric Sulfate•5H$_2$O | 0.025 |
| | Na2 EDTA•2H$_2$O | 37.26 |
| | Ferrous Sulfate•7H$_2$O | 27.8 |
| | Magnesium Sulfate, Anhydrous | 90.372 |
| | Manganese Sulfate•H$_2$O | 18.9 |
| | Molybdic Acid (Sodium Salt)•2H$_2$O | 0.25 |
| | Potassium Nitrate | 950 |
| | Potassium Phosphate, Monobasic | 68 |
| | Zinc Sulfate•7H$_2$O | 10 |
| | D-Biotin | 0.05 |
| | Folic Acid | 0.5 |
| | Glycine (Free Base) | 2 |
| | myo-Inositol | 100 |
| | Nicotinic Acid (Free Acid) | 5 |
| | Pyridoxine•HCl | 0.5 |
| | Thiamine•HCl | 0.5 |

5.2 Optimum pH Level

In order to determine the optimum pH condition required for mass-culture, the yield in ½MS and MS media was examined according to each pH level to establish the optimum pH condition. 20 ml of each media was put into a 300 ml flask, 0.8 g of hairy root H20 was inoculated, and cultured at a known optimum pH 5.8 and, at each different pH 5.0, 7.0, and 8.0 for 10 days. The yield was higher at pH 8.0 than at the known optimum pH 5.8. Accordingly, pH 8.0 was selected as the optimum pH condition for mass-production (FIG. 24).

5.3 Selection of Optimal Sucrose Concentration

To determine the optimal concentration of sucrose used as an energy source in media ingredients, MS media was treated with various concentrations of sucrose such as 0 g/L, 7.5 g/L, 15 g/L, 30 g/L, and 60 g/L, and then the hairy roots were cultured in the liquid media. The yield of the hairy root was examined to determine the optimal concentration of sucrose. It was found that there was no difference in yield between the concentrations of 15 g/L and 30 g/L. Accordingly, the concentration of 15 g/L was determined as the optimal concentration to minimize production cost (FIG. 25).

5.4 Applicability of Selected Liquid Culture Condition to Mass-Production System 80 g of HA hairy root were inoculated in an 18 L bioreactor containing MS media (pH 8.0), and then cultured at 24° C. under a fluorescent light (500 or less Lux, 10 hrs light/14 hrs dark) for 14 days. The culture condition selected in Examples 5.1 to 5.3 was applied to an 18 L mass production system. As a result, the yield was increased from 80 g to 913 g to confirm the possibility of mass-production (FIG. 26).

6. Expression Level of HA Protein

In order to examine the expression level of HA in hairy root, an Ag ELISA was performed. HA protein expressed in bacteria was used as a positive control, and the HA expression level was measured using the above mentioned HA Ag ELISA.

First, proteins were extracted from 50 mg of freeze-dried hairy root using an extraction buffer at 4° C. for 3 hrs, and then immediately centrifuged at 10,000×g. A total volume was adjusted to 800 µl using the extraction buffer. For analysis, 100 µl of 2-fold serial dilutions were used. The HA protein expressed in bacteria was subjected to Coomassie staining to determine its concentration. 1.56 µl of bacterial recombinant HA protein was subjected to 2-fold serial dilutions with the extraction buffer, and loaded in a plate to perform the HA Ag ELISA. The Ag ELISA was performed in the same manner as in 3.1, and all samples were performed twice.

Based on the sample extracted from the air-dried sample, the standard OD value of trangenic—>expressed HA protein, of which concentration was known, was substituted with the OD value measured in the mock transgenic hairy root to calculate its concentration. Then, background was subtracted from the OD value of HA transgenic hairy root. That is, 1.173 μg calculated from the mock transgenic hairy root was subtracted from 2.103 μg calculated from HA transgenic hairy root to give 0.93 μg. 100 μl was used from the total 800 μl of extract, and thus 50 mg of transgenic hairy root contained 7.44 μg of HA protein. Accordingly, it can be seen that the hairy root contains the HA protein of 0.15 μg/mg as dry weight. Its content in water-soluble proteins was quantified to give 0.2% expression (FIG. 27).

7. Animal Test of HA

In vivo test was performed with the hairy root, of which HA expression was confirmed above. 6~8-week-old female BALB/c mice were purchased, and four mice were maintained in individual cages, and their blood was collected at 1 week before performing immunization. The freeze-dried hairy root was orally administered to mice. In brief, mice were first fasted for 8 hrs or more with free access to water. At 30 min before immunization, 100 μl of 1.5% sodium bicarbonate was orally administered. Each of 1 mg and 5 mg of freeze-dried hairy root was diluted with 350 mM sodium bicarbonate to a total volume of 100 μl, and orally administered to two mice in a wild-type hairy root group and two mice in the transgenic hairy root group using a zonde needle Immunization was performed at 7-day intervals, and serum was isolated on day 8 after the last immunization. Feces were collected on day 3 after the last immunization (FIG. 28).

8. HA-Specific Antibody ELISA 8.1 Serum IgG ELISA

ELISA was performed to detect HA-specific antibody from the serum samples obtained after immunization. First, an ELISA plate was coated with the protein expressed in bacteria, and then the serum sample was added as a primary antibody. As a secondary antibody, anti-mouse IgG HRP was used. In this connection, the plate was coated with the protein in a concentration of 3 μg/ml, and the sample was diluted at a ratio of 1:50. The secondary antibody was diluted at a ratio of 1:2,000. As shown in the figure, it was found that in the group treated with HA transgenic hairy root, the HA-specific antibody was more highly induced than in the group treated with mock transgenic hairy root. There was no significant difference between the group treated with 5 mg and a negative group (FIG. 29).

8.2 Fecal IgA ELISA 100 mg of feces were suspended with 1 ml of extraction buffer (PBS-0.01% sodium azide with general protease inhibitor cocktail and 5% FBS) to prepare fecal samples. The suspension was vortexed at 4° C. for 30 min, and then centrifuged at 4° C. and 16,000×g. The supernatant was collected, and immediately subjected to ELISA. The supernatant was loaded without dilution, and the process was performed in the same manner as mentioned above. As a secondary antibody, an HRP-anti-mouse IgA was used at a 1:2,000 dilution. As shown in FIG. 30, in the group treated with 1 mg of HA transgenic hairy root, the induction of HA-specific antibody was about twice as high as the control group.

The invention claimed is:

1. The vector for plant transformation, pBSNB-TEV, as shown in FIG. 4.

2. A method for producing a recombinant foreign protein in a plant, said method comprising the steps of:
   i) making an expression vector by introducing a nucleic acid molecule encoding the foreign protein into the vector of claim 1;
   ii) transforming a plant with the expression vector; and
   iii) growing the transformed plant to produce the protein.

3. The method according to claim 2, wherein the transformation is performed using *Agrobacterium* comprising the expression vector.

4. The method according to claim 2, wherein the plant is selected from the group consisting of rice (*Oryza sativa*), barley (*Hordeum sativum*), wheat (*Triticum aestivum* or *Triticum vulgare*), potato (*Solanum tuberosum*), sweet potato (*Ipomoea batatas*), cucumber (*cucumis sativus*), and Korean melon (*Cucumis melo*).

5. The method according to claim 4, wherein the plant is Korean melon.

6. The method according to claim 5, wherein the protein is produced in the hairy roots of the Korean melon.

7. The method of claim 2, wherein the foreign protein is a pathogenic antigen protein.

8. The method according to claim 7, wherein the antigen protein is a surface protein of avian influenza virus.

9. The method according to claim 8, wherein the surface protein is hemagglutinin (HA) or neuramidase (NA).

10. The method according to claim 7, wherein the antigen protein is a nucleoprotein (NP), an RNA polymerase protein polymerase basic protein 2 (PB2), or a polymerase acid protein (PA) of avian influenza virus.

11. A vector for plant transformation comprising a nucleic acid molecule encoding a surface protein of avian influenza virus, HA (hemagglutinin) or NA (neuraminidase) ligated into a polycloning site of the vector of claim 1.

12. A plant transformed with the vector of claim 11.

13. A part of the plant according to claim 12, wherein the part is a hairy root, and wherein the plant is selected from the group consisting of rice (*Oryza sativa*), barley (*Hordeum sativum*), wheat (*Triticum aestivum* or *Triticum vulgare*), potato (*Solanum tuberosum*), sweet potato (*Ipomoea batatas*), cucumber (*cucumis sativus*), and Korean melon (*Cucumis melo*).

14. An oral avian influenza vaccine comprising the part of the plant according to claim 13.

15. The oral vaccine according to claim 14, wherein the part of the plant is an air-dried hairy root of Korean melon.

16. A method for mass-producing the part of the plant of claim 13, wherein the plant is liquid-cultured in MS or B5 medium at pH 7 to 8.

17. The method according to claim 16, wherein the medium contains sucrose in a concentration of 10 to 20 g/L.

18. A method for preparing a reagent for diagnosing avian influenza virus infection, comprising the step of isolating the surface protein from the transgenic plant of claim 12.

* * * * *